United States Patent
Garcia

(10) Patent No.: US 10,633,710 B2
(45) Date of Patent: Apr. 28, 2020

(54) METHODS FOR CHARACTERIZING CANCER

(71) Applicant: ARIZONA BOARD OF REGENTS ON BEHALF OF THE UNIVERSITY OF ARIZONA, Tucson, AZ (US)

(72) Inventor: Joe G. N. Garcia, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/504,168

(22) PCT Filed: Aug. 14, 2015

(86) PCT No.: PCT/US2015/045191
§ 371 (c)(1),
(2) Date: Feb. 15, 2017

(87) PCT Pub. No.: WO2016/025785
PCT Pub. Date: Feb. 18, 2016

(65) Prior Publication Data
US 2017/0275701 A1 Sep. 28, 2017

Related U.S. Application Data

(60) Provisional application No. 62/037,744, filed on Aug. 15, 2014.

(51) Int. Cl.
| | | |
|---|---|---|
| *C12Q 1/6886* | (2018.01) | |
| *C12Q 1/6883* | (2018.01) | |
| *C12N 15/10* | (2006.01) | |
| *C12Q 1/6806* | (2018.01) | |
| *C12Q 1/6813* | (2018.01) | |
| *C12Q 1/6841* | (2018.01) | |
| *C12Q 1/686* | (2018.01) | |
| *G01N 30/72* | (2006.01) | |

(52) U.S. Cl.
CPC .......... *C12Q 1/6886* (2013.01); *C12N 15/10* (2013.01); *C12Q 1/6806* (2013.01); *C12Q 1/686* (2013.01); *C12Q 1/6813* (2013.01); *C12Q 1/6841* (2013.01); *G01N 30/72* (2013.01); *C12Q 1/6883* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2009/0092983 A1 | 4/2009 | Birnbaum et al. |
| 2010/0009357 A1* | 1/2010 | Nevins ............... C12Q 1/6886 435/6.12 |
| 2011/0195848 A1 | 8/2011 | Roopra et al. |
| 2012/0225433 A1 | 9/2012 | Cobleigh et al. |

FOREIGN PATENT DOCUMENTS

WO  WO 2016025785  2/2016

OTHER PUBLICATIONS

Affymetrix NetAffx Query for the Human Genome U133 Plus 2.0 Array, available via URL: <affymetrix.com/analysis/netaffx/xmlquery.affx?netaffx=netaffx4_annot>, printed on Oct. 24, 2018, 8 pages.*
Palmer et al. BMC Genomics. 2006. 7:115.*
Hanke et al. Clinical Chemistry. 2007. 53: 2070-2077.*
Murphy et al. Pathology, 2005, vol. 37(4), pp. 271-277.*
Badea et al., "Combined gene expression analysis of whole-tissue and microdissected pancreatic ductal adenocarcinoma identifies genes specifically overexpressed in tumor epithelia." Hepatogastroenterology. Nov.-Dec. 2008;55(88):2016-27.
Bastarrachea et al., "Obesity as an adverse prognostic factor for patients receiving adjuvant chemotherapy for breast cancer." Ann Intern Med. Jan. 1, 1994;120(1):18-25.
Botling et al., "Biomarker discovery in non-small cell lung cancer: integrating gene expression profiling, meta-analysis, and tissue microarray validation." Clin Cancer Res. Jan. 1, 2013;19(1):194-204.
Buldak et al., "Visfatin affects redox adaptative responses and proliferation in Me45 human malignant melanoma cells: an in vitro study." Oncol Rep. Feb. 2013;29(2):771-8.
Cheranova et al., "Pleiotropic functions of pre-B-cell colony-enhancing factor (PBEF) revealed by transcriptomics of human pulmonary microvascular endothelial cells treated with PBEFsiRNA." Genes Cells. May 2012;17(5):420-30.
Chini et al., "Targeting of NAD metabolism in pancreatic cancer cells: potential novel therapy for pancreatic tumors." Clin Cancer Res. Jan. 1, 2014;20(1):120-30.

(Continued)

*Primary Examiner* — Carla J Myers
(74) *Attorney, Agent, or Firm* — Casimir Jones, S.C.; Tanya A. Arenson

(57) ABSTRACT

A method of identifying gene expression associated with recurrence free survival in a subject with cancer, comprising: a) assaying a sample from a subject diagnosed with cancer for the presence of altered gene expression of one or more genes selected from the group consisting of ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, and ZMIZ2; and b) identifying an outcome of decreased likelihood of recurrence free survival when altered gene expression relative to the level in a non-cancerous sample is present.

4 Claims, 12 Drawing Sheets

(56) References Cited

OTHER PUBLICATIONS

Dahl et al., "Visfatin/NAMPT: a multifaceted molecule with diverse roles in physiology and pathophysiology." Annu Rev Nutr. Aug. 21, 2012;32:229-43.

Dawson et al., "Analysis of circulating tumor DNA to monitor metastatic breast cancer." N Engl J Med. Mar. 28, 2013;368(13):1199-209.

Diehl et al., "Circulating mutant DNA to assess tumor dynamics." Nat Med. Sep. 2008;14(9):985-90.

Edgar et al., "Gene Expression Omnibus: NCBI gene expression and hybridization array data repository." Nucleic Acids Res. Jan. 1, 2002;30(1):207-10.

Edwards et al., "Infiltrating ductal carcinoma of the breast: the survival impact of race." J Clin Oncol. Aug. 1998;16(8):2693-9.

Elledge et al., "Tumor biologic factors and breast cancer prognosis among white, Hispanic, and black women in the United States." J Natl Cancer Inst. May 4, 1994;86(9):705-12.

Fry et al., "Ten-year survey of lung cancer treatment and survival in hospitals in the United States: a national cancer data base report." Cancer. Nov. 1, 1999;86(9):1867-76.

Gail et al., "Prognostic factors in patients with resected stage I non-small cell lung cancer. A report from the Lung Cancer Study Group." Cancer. Nov. 1, 1984;54(9):1802-13.

Gautier et al., "affy—analysis of Affymetrix GeneChip data at the probe level." Bioinformatics. Feb. 12, 2004;20(3):307-15.

Harpole et al., "A prognostic model of recurrence and death in stage I non-small cell lung cancer utilizing presentation, histopathology, and oncoprotein expression." Cancer Res. Jan. 1, 1995;55(1):51-6.

Hatzis et al., "A genomic predictor of response and survival following taxane-anthracycline chemotherapy for invasive breast cancer." JAMA. May 11, 2011;305(18):1873-81.

Horio et al., "Prognostic significance of p53 mutations and 3p deletions in primary resected non-small cell lung cancer." Cancer Res. Jan. 1, 1993;53(1):1-4.

Ichinose et al., "Is T factor of the TNM staging system a predominant prognostic factor in pathologic stage I non-small-cell lung cancer ? A multivariate prognostic factor analysis of 151 patients." J Thorac Cardiovasc Surg. Jul. 1993;106(1):90-4.

Jemal et al., "Global cancer statistics." CA Cancer J Clin. Mar.-Apr. 2011;61(2):69-90.

Jia et al., "Pre-B cell colony-enhancing factor inhibits neutrophil apoptosis in experimental inflammation and clinical sepsis." J Clin Invest. May 2004;113(9):1318-27.

Kaisermann et al., "Evolving features of lung adenocarcinoma in Rio de Janeiro, Brazil." Oncol Rep. Jan.-Feb. 2001;8(1):189-92.

Kanehisa et al., "The KEGG resource for deciphering the genome." Nucleic Acids Res. Jan. 1, 2004;32(Database issue):D277-80.

Ko et al., "Expression profiling of ion channel genes predicts clinical outcome in breast cancer." Mol Cancer. Sep. 22, 2013;12(1):106.

Ko et al., "Ion channel gene expression in lung adenocarcinoma: potential role in prognosis and diagnosis." Ion channel gene expression in lung adenocarcinoma: potential role in prognosis and diagnosis.

Lee et al., "Prediction of recurrence-free survival in postoperative non-small cell lung cancer patients by using an integrated model of clinical information and gene expression." Clin Cancer Res.Nov. 15, 2008;14(22):7397-404.

Menssen et al., "The c-MYC oncoprotein, the NAMPT enzyme, the SIRT1-inhibitor DBC1, and the SIRT1 deacetylase form a positive feedback loop." Proc Natl Acad Sci U S A. Jan. 24, 2012;109(4):E187-96.

Moreno-Vinasco et al., "Nicotinamide phosphoribosyltransferase inhibitor is a novel therapeutic candidate in murine models of inflammatory lung injury." Am J Respir Cell Mol Biol. Aug. 2014;51(2):223-8.

Oita et al., "Visfatin induces oxidative stress in differentiated C2C12 myotubes in an Akt- and MAPK-independent, NFkB-dependent manner." Pflugers Arch. Mar. 2010;459(4):619-30.

Okayama et al., "Identification of genes upregulated in ALK-positive and EGFR/KRAS/ALK-negative lung adenocarcinomas." Cancer Res. Jan. 1, 2012;72(1):100-11.

Pairolero et al., "Postsurgical stage I bronchogenic carcinoma: morbid implications of recurrent disease." Ann Thorac Surg. Oct. 1984;38(4):331-8.

Pitroda et al., "Tumor endothelial inflammation predicts clinical outcome in diverse human cancers." PLoS One. 2012;7(10):e46104.

Rodenhuis et al., "Mutational activation of the K-ras oncogene. A possible pathogenetic factor in adenocarcinoma of the lung." N Engl J Med. Oct. 8, 1987;317(15):929-35.

Roggli et al., "Lung cancer heterogeneity: a blinded and randomized study of 100 consecutive cases." Hum Pathol. Jun. 1985;16(6):569-79.

Sabatier et al., "A gene expression signature identifies two prognostic subgroups of basal breast cancer." Breast Cancer Res Treat. Apr. 2011;126(2):407-20.

Samal et al., "Cloning and characterization of the cDNA encoding a novel human pre-B-cell colony-enhancing factor." Mol Cell Biol. Feb. 1994;14(2):1431-7.

Sanchez-Palencia et al., "Gene expression profiling reveals novel biomarkers in nonsmall cell lung cancer." Int J Cancer. Jul. 15, 2011;129(2):355-64.

Sato et al., "Human lung epithelial cells progressed to malignancy through specific oncogenic manipulations." Mol Cancer Res. Jun. 2013;11(6):638-50.

Shackelford et al., "Nicotinamide phosphoribosyltransferase in malignancy: a review." Genes Cancer. Nov. 1990;4(11-12):447-56.

Slebos et al., "K-ras oncogene activation as a prognostic marker in adenocarcinoma of the lung." N Engl J Med. Aug. 30, 1990;323(9):561-5.

Storey "A direct approach to false discovery rates" Journal of the Royal Statistical Society Series B—Statistical Methodology 64, 2002, 479-498.

Takise et al., "Histopathologic prognostic factors in adenocarcinomas of the peripheral lung less than 2 cm in diameter." Cancer. May 15, 1988;61(10):2083-8.

Taylor et al. "The 'miss rate' for the analysis of gene expression data." Biostatistics. Jan. 2005;6(1):111-7.

Tusher et al., "Significance analysis of microarrays applied to the ionizing radiation response." Proc Natl Acad Sci U S A. Apr. 24, 2001;98(9):5116-21.

Uddin et al., "Genome-wide expression analysis of Middle Eastern colorectal cancer reveals FOXM1 as a novel target for cancer therapy." Am J Pathol. Feb. 2011;178(2):537-47.

Van Der Veer et al., "Extension of human cell lifespan by nicotinamide phosphoribosyltransferase." J Biol Chem. Apr. 13, 2007;282(15):10841-5.

Venet et al., "Most random gene expression signatures are significantly associated with breast cancer outcome." PLoS Comput Biol. Oct. 2011;7(10):e1002240.

Wang et al., "Gene-expression profiles to predict distant metastasis of lymph-node-negative primary breast cancer." Lancet. Feb. 19-25, 2005;365(9460):671-9.

Wang et al., "SIRT1 deacetylase promotes acquisition of genetic mutations for drug resistance in CML cells." Oncogene. Jan. 31, 2013;32(5):589-98.

Williams et al., "Survival of patients surgically treated for stage I lung cancer." J Thorac Cardiovasc Surg. Jul. 1981;82(1):70-6.

Wu et al. "A model-based background adjustment for oligonucleotide expression arrays." Journal of the American Statistical Association, 2004, 99, 909-917.

Ye et al., Pre-B-cell colony-enhancing factor as a potential novel biomarker in acute lung injury: Am J Respir Crit Care, 2005, Med 171, 361-370.

Zhang et al., "Enzymes in the NAD+ salvage pathway regulate SIRT1 activity at target gene promoters." J Biol Chem. Jul. 24, 2009;284(30):20408-17.

Zhou et al., "Expression of nicotinamide phosphoribosyltransferase-influenced genes predicts recurrence-free survival in lung and breast cancers." Sci Rep. Aug. 22, 2014;4:6107. 8 pages.

(56) References Cited

OTHER PUBLICATIONS

International Search Report of related PCT/US2015/045191, dated Nov. 20, 2015, 15 pages.

* cited by examiner

METHODS FOR CHARACTERIZING CANCER

CROSS-REFERENCE TO RELATED APPLICATIONS

The present application is a U.S. 371 national phase entry of International Patent Application No. PCT/US2015/045191, filed Aug. 14, 2015, which claims priority to U.S. Provisional Patent Application Ser. No. 62/037,744, filed Aug. 15, 2014, the disclosure of which is herein incorporated by reference in their entireties.

FIELD OF THE INVENTION

The present disclosure relates to methods of characterizing cancer. In particular, the present disclosure relates to genes associated with recurrence-free survival in cancer (e.g., breast or lung cancer).

BACKGROUND OF THE INVENTION

Lung cancer remains the leading cause of cancer death in industrialized countries. About 75 percent of lung cancer cases are categorized as non-small cell lung cancer (e.g., adenocarcinomas), and the other 25 percent are small cell lung cancer. Lung cancers are characterized in to several stages, based on the spread of the disease. In stage I cancer, the tumor is only in the lung and surrounded by normal tissue. In stage II cancer, cancer has spread to nearby lymph nodes. In stage III, cancer has spread to the chest wall or diaphragm near the lung, or to the lymph nodes in the mediastinum (the area that separates the two lungs), or to the lymph nodes on the other side of the chest or in the neck. This stage is divided into IIIA, which can usually be operated on, and stage IIIB, which usually cannot withstand surgery. In stage IV, the cancer has spread to other parts of the body.

Most patients with non-small cell lung cancer (NSCLC) present with advanced stage disease, and despite recent advances in multi-modality therapy, the overall ten-year survival rate remains dismal at 8-10% (Fry et al., Cancer 86:1867 [1999]). However, a significant minority of patients, approximately 25-30%, with NSCLC have pathological stage I disease and are usually treated with surgery alone. While it is known that 35-50% of patients with stage I disease will relapse within five years (Williams et al., Thorac. Cardiovasc. Surg. 82:70 [1981]; Pairolero et al., Ann, Thorac. Surg. 38:331 [1984]), it is not currently possible to identify which specific patients are at high risk of relapse.

Adenocarcinoma is currently the predominant histologic subtype of NSCLC (Fry et al., supra; Kaisermann et al., Brazil Oncol. Rep. 8:189 [2001]; Roggli et al., Hum. Pathol. 16:569 [1985]). While histopathological assessment of primary lung carcinomas can roughly stratify patients, there is still an urgent need to identify those patients who are at high risk for recurrent or metastatic disease by other means. Previous studies have identified a number of preoperative variables that impact survival of patients with NSCLC (Gail et al., Cancer 54:1802 1984]; Takise et al., Cancer 61:2083 [1988]; Ichinose et al., J. Thorac. Cardiovasc. Surg. 106:90 [1993]; Harpole et al., Cancer Res. 55:1995]). Tumor size, vascular invasion, poor differentiation, high tumor proliferate index, and several genetic alterations, including K-ras (Rodenhuis et al., N. Engl. J. Med. 317:929 [1987]; Slebos et al., N. Engl. J. Med. 323:561 [1990]) and p53 (Harpole et al., supra; Horio et al., Cancer Res. 53:1 [1993]) mutation, have been reported as prognostic indicators.

Tumor stage is an important predictor of patient survival, however, much variability in outcome is not accounted for by stage alone, as is observed for stage I lung adenocarcinoma which has a 65-70% five-year survival (Williams et al., supra; Pairolero et al., supra). Current therapy for patients with stage I disease usually consists of surgical resection and no additional treatment (Williams et al., supra; Pairolero et al., supra). The identification of a high-risk group among patients with stage I disease would lead to consideration of additional therapeutic intervention for this group, as well as leading to improved survival of these patients.

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of estrogen receptor (ER) and progesterone receptor (PR) levels.

Prognosis and selection of therapy are influenced by the age of the patient, stage of the disease, pathologic characteristics of the primary tumor including the presence of tumor necrosis, ER and PR levels in the tumor tissue, HER2 overexpression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor downregulators), and monoclonal antibody treatment (e.g., against HER2). They may be used separately or, most often, in different combinations.

There is a need for additional diagnostic and treatment options, particularly treatments customized to a patient's tumor.

SUMMARY OF THE INVENTION

The present disclosure relates to methods of characterizing cancer. In particular, the present disclosure relates to genes associated with recurrence-free survival in cancer (e.g., breast or lung cancer).

Embodiments of the present disclosure provide a method of identifying gene expression associated with recurrence free survival in a subject with cancer, comprising: a) assaying a sample from a subject diagnosed with cancer for the presence of altered gene expression of one or more (e.g., 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, or all) genes selected from ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X, MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, or ZMIZ2; and b) identifying an outcome of decreased likelihood of recurrence free survival when altered gene expression relative to the level in a non-cancerous sample is present. In some embodiments, the cancer is a solid tumor (e.g., lung cancer or breast cancer). In some embodiments, the gene expression is increased or decreased relative to the level in non-cancerous samples. In some embodiments, the sample is, for example, tissue, blood, plasma, serum, lung cells, or breast cells. In some embodiments, the detecting comprises forming a complex between the genes and a nucleic acid primer, probe, or pair of primers that specifically bind to the genes. In some embodiments, a cut-off score of gene expression level is used to determine a decreased likelihood of recurrence free survival. For example, in some embodiment, a score above zero is indicative of a reduced survival.

Further embodiments provides a composition comprising at least two complexes comprising a nucleic acid encoding a gene selected from two or more (e.g., 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, or all) genes selected from ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X, MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, or ZMIZ2; and at least two distinct nucleic acid primers or probes that specifically hybridize to the two or more genes.

Additional embodiments provide a kit, comprising: reagents for detecting altered gene expression levels of two or more (e.g., 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, or all) genes selected from ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X, MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, or ZMIZ2. In some embodiments, the primers or probes are at least 8, 10, or 20 nucleic acids in length.

Yet other embodiment provide a system, comprising: a) a computer processor; and b) computer software configured to analyze information on the presence of altered gene expression of two or more (e.g., 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, or all) genes selected from ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X, MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, or ZMIZ2; and determine the likelihood of recurrence free survival in a subject diagnosed with cancer (e.g., breast or lung cancer) based on the presence of the altered levels of gene expression.

Other embodiments provide method of identifying gene expression in a subject with cancer, comprising: a) assaying a sample (e.g., cancer cell or tissue) from a subject diagnosed with cancer for the presence of altered gene expression of one or more (e.g., 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, 31, 32, 33, 34, 35, 36, 37, 38, or all) genes selected from ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X, MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, or ZMIZ2.

Additional embodiments are described herein.

DEFINITIONS

Figure 1:
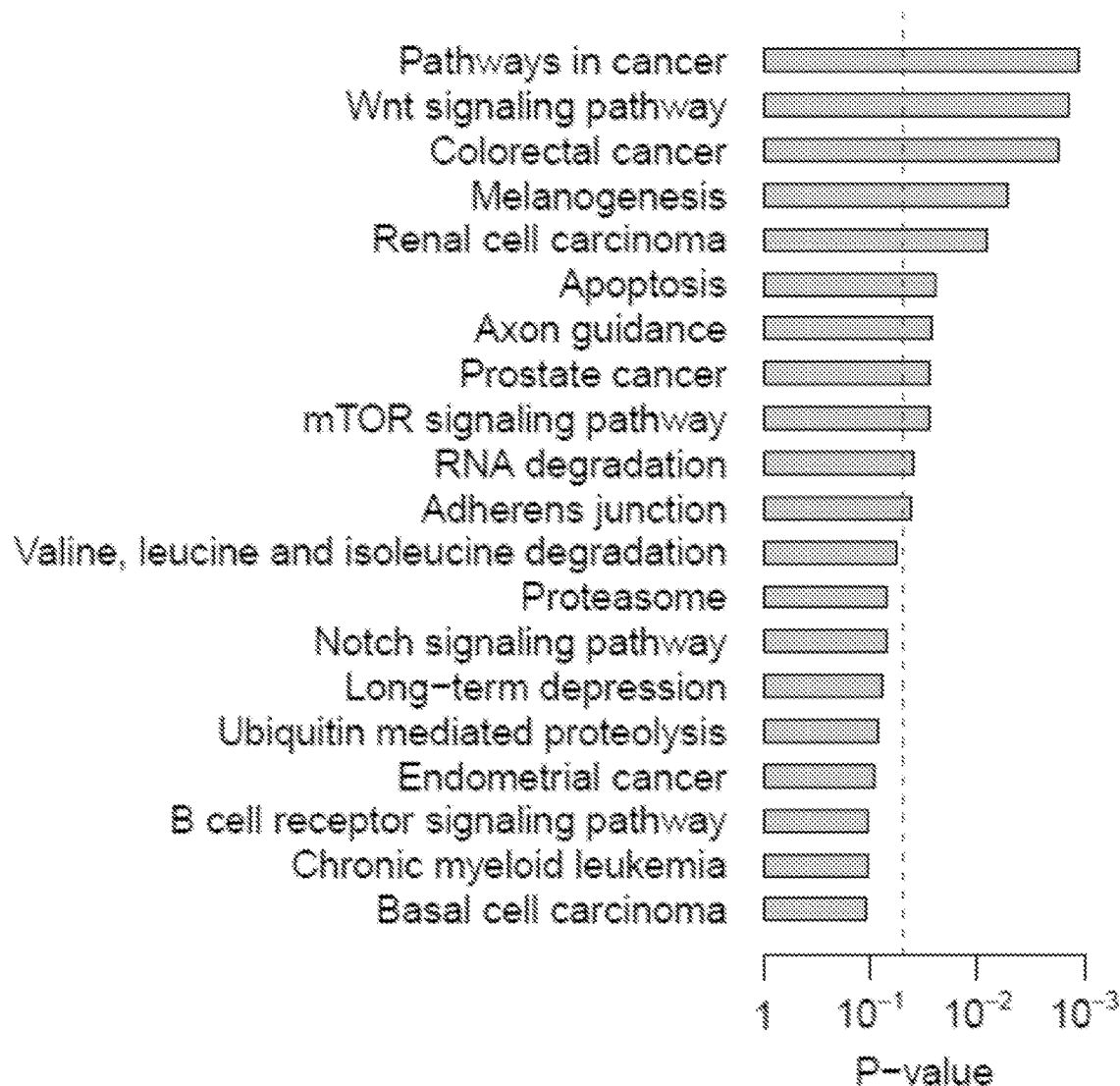
FIG. 1 shows the top 20 KEGG pathway terms associated with the NAMPT (also known as visfatin and PBEF) influenced genes.

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., humans).

The term "diagnosed," as used herein, refers to the recognition of a disease by its signs and symptoms, or genetic analysis, pathological analysis, histological analysis, and the like.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, those described herein As used herein, the term "characterizing cancer in a subject" refers to the identification of one or more properties of a cancer sample (e.g., including but not limited to, the presence of cancerous tissue, the presence or absence of altered levels of expression of the gene described herein, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., biopsy samples), cells, and gases. Biological samples include blood products, such as plasma, serum and the like. Such examples are not however to be construed as limiting the sample types applicable to the present invention.

DETAILED DESCRIPTION OF THE INVENTION

The present disclosure relates to methods of characterizing cancer. In particular, the present disclosure relates to genes associated with recurrence-free survival in cancer (e.g., breast or lung cancer).

Nicotinamide phosphoribosyltransferase (NAMPT) encodes a protein NAMPT (also known as visfatin, and pre-B cell colony-enhancing factor 1 (PBEF1), that catalyzes the condensation of nicotinamide with 5-phosphoribosyl-1-pyrophosphate to yield nicotinamide mononucleotide, and it is the rate-limiting enzyme in the salvage pathway of nicotinamide adenine dinucleotide (NAD) synthesis (Dahl, T. B., et al., *Annu Rev Nutr* 32, 229-243, (2012)). This multifunctional enzyme was first cloned from human lymphocytes, and named pre-B cell colony-enhancing factor as a secreted cytokine (Samal, B. et al. *Mol Cell Biol* 14, 1431-1437, (1994)). NAMPT was further confirmed as a pro-inflammatory cytokine (Ye, S. Q. et al. Pre-B-cell colony-enhancing factor as a potential novel biomarker in acute lung injury. Am J Respir Crit Care Med 171, 361-370, (2005)) that inhibits neutrophil apoptosis (Jia, S. H. et al. *J Clin Invest* 113, 1318-1327, (2004)) and exerts endotoxin-like responses to trigger NFκB signaling pathways (Oita, R. C., *Pflugers Arch* 459, 619-630, (2010)). Given the dual intracellular enzymatic activity (iNAMPT) and extracellular proinflammatory cytokine characteristics (eNAMPT), NAMPT was implicated in many important biological processes, including metabolism, stress response, apoptosis and aging (Dahl et al., supra), the majority of which are closely related to carcinogenesis signaling.

Secreted NAMPT or eNAMPT is elevated in plasma in a variety of human cancer types including gastric, endometrial, hepatocellular, colorectal, and breast cancers (Shackelford, et al., *Genes Cancer* 4, 447-456, (2014)). The inflammatory response of eNAMPT on tissues promotes tumor proliferation and redox adaptative responses (Buldak, R. J. et al. *Oncology reports* 29, 771-778, (2013)). Moreover, as an enzyme, intracellular NAMPT or iNAMPT is responsible for regeneration of intracellular $NAD^+$, which is a multi-functional co-factor in many cellular events, such as transcriptional regulation, longevity and caloric-restriction responses, cell cycle progression, apoptosis, DNA repair, circadian rhythms, chromatin dynamics regulation, telomerase activity, closely related to cancer pathogenesis (Shackelford et al, supra). NAMPT enzymatic activity is inhibited by the highly specific, noncompetitive inhibitor, FK-866 (alternative names: AP0866, Daporinad, K 22.175, WK175), (Moreno-Vinasco, L. et al. *Am J Respir Cell Mol Biol*, (2014)). Additional studies determined that FK-866 produced premature senescence, linked to decreased activity of the $NAD^+$-dependent enzyme, SIRT1 (van der Veer, E. et al. *J Biol Chem* 282, 10841-10845, (2007)).

Experiment described herein identified NAMPT-influenced genes implicated in cancer pathobiology. First, differentially expressed genes were identified utilizing microarray data from two independent human cell lines (primary and cancer cells) and wild-type (WT) cells and NAMPT knock down (KD) cells. These differentially-expressed genes were denoted as NAMPT-influenced genes with gene ontology analysis indicating enriched cancer related pathways. Second, a prognostic gene signature derived from the NAMPT-influenced genes was developed and expression compared in normal and colon, lung, pancreatic, and thyroid cancers. Thirty-nine NAMPT-influenced genes were identified as being commonly differentially expressed in tumor tissues and comprised a multi-molecular cancer outcome predictor. The studies indicate one or more (e.g., all) of the genes in this molecular signature effectively predicts recurrence-free survival in lung and breast cancer in a manner independent of standard clinical and pathological prognostic factors.

Accordingly, embodiments of the present disclosure provide research, screening, diagnostic, and prognostic methods for characterizing cancer (e.g., breast or lung cancer) and identifying altered gene expression in samples from a subject diagnosed with cancer (e.g., a cancer cell or tissue sample). The present disclosure is not limited to the detection of a specific cancer. The gene signatures described herein find use in the diagnosis, screening, and research of a variety of solid tumors. Examples include, but are not limited to, lung, breast, thyroid, colorectal, liver, kidney, prostate, stomach, and pancreatic cancers.

I. Diagnostic and Screening Methods

As described above, embodiments of the present invention provide diagnostic and screening methods that utilize the detection of altered gene expression levels of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or all 39) of those shown in table 1 (e.g., ADK, AP2B1, AVL9, CANX, DBT, DHRS7, DONSON, FAM190B, FGFR1, FOXN3, FZD5, GGH, GM2A, IGFBP5, ITSN2, LAMC1, LIFR, METTL7A, MT1F, MT1G, MT1P2, MT1X, MT2A, NAB1, NCOA1, NCOR1, PAPOLA, PPME1, PPP1R13L, PRKAR2A, RABEP1, RBBP8, SGPL1, SIRT1, SNX2, SREK1, TAF1B, TMED5, or ZMIZ2). Exemplary, non-limiting methods are described below.

Any patient sample suspected of containing the genes may be tested according to methods of embodiments of the present invention. By way of non-limiting examples, the sample may be tissue (e.g., a breast or lung biopsy sample), blood, urine, or a fraction thereof (e.g., plasma, serum, cells).

In some embodiments, the patient sample is subjected to preliminary processing designed to isolate or enrich the sample for the genes or cells that contain the gene. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

In some embodiments, gene expression is monitored in circulating tumor DNA (See e.g., Dawson, S. J. et al. Analysis of circulating tumor DNA to monitor metastatic breast cancer. N Engl J Med 368, 1199-209 (2013); Diehl, F. et al. Nat Med 14, 985-90 (2008)).

In some embodiments, expression levels of the genes are detected along with other markers in a multiplex or panel format. Markers are selected for their predictive value alone or in combination with the levels of genes expression. Markers for other cancers, diseases, infections, and metabolic conditions are also contemplated for inclusion in a multiplex or panel format.

i. DNA and RNA Detection

The levels of gene expression of the genes described herein are detected using a variety of nucleic acid techniques known to those of ordinary skill in the art, including but not limited to: nucleic acid sequencing; nucleic acid hybridization; and, nucleic acid amplification.

1. Sequencing

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbial.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbial.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing (see, e.g., Astier et al., J. Am. Chem. Soc. 2006 Feb. 8; 128(5):1705-10, herein incorporated by reference) is utilized. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety) is utilized. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs.

The accuracy for homopolymer repeats of 5 repeats in length is ~98%. The benefits of ion semiconductor sequencing are rapid sequencing speed and low upfront and operating costs.

Stratos Genomics, Inc. sequencing involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. Nos. 11/671,956; 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, altered gene expression is detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human cells (e.g., breast or endometrial cells). Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121, 489 and 6,573,043. All of these references are hereby incorporated by reference in their entirety and may be used along with similar references in the art and with the information provided in the Examples section herein to establish procedural steps convenient for a particular laboratory.

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., those described in table 1) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

4. Amplification

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

5. Protein Detection

In some embodiments, altered levels gene expression are detected by detected altered levels of polypeptides encoded by the genes (e.g., using immunoassays or mass spectrometry).

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Mass spectrometry has proven to be a valuable tool for the determination of molecular structures of molecules of many kinds, including biomolecules, and is widely practiced today. Purified proteins are digested with specific proteases (e.g. trypsin) and evaluated using mass spectrometry. Many alternative methods can also be used. For instance, either matrix-assisted laser desorption/ionization (MALDI) or electrospray ionization (ESI) mass spectrometric methods can be used. Furthermore, mass spectroscopy can be coupled with the use of two-dimensional gel electrophoretic separation of cellular proteins as an alternative to comprehensive pre-purification. Mass spectrometry can also be coupled with the use of peptide fingerprint database and various searching algorithms. Differences in post-translational modification, such as phosphorylation or glycosylation, can also be probed by coupling mass spectrometry with the use of various pretreatments such as with glycosylases and phosphatases. All of these methods are to be considered as part of this application.

In some embodiments, electrospray ionisation quadrupole mass spectrometry is utilized to detect polypeptide levels (See e.g., U.S. Pat. No. 8,658,396; herein incorporated by reference in its entirety).

6. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy, blood, urine, tissue, cell, or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., gene expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of altered levels of gene expression of the genes in Table 1) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

6. Compositions & Kits

Compositions for use in the diagnostic methods described herein include, but are not limited to, probes, amplification oligonucleotides, and the like. In some embodiments, kits include all components necessary, sufficient or useful for detecting the markers described herein (e.g., reagents, controls, instructions, etc.). The kits described herein find use in research, therapeutic, screening, and clinical applications.

The probe and antibody compositions of the present invention may also be provided in the form of an array.

In some embodiments, the present invention provides one or more nucleic acid probes or primers having 8 or more (e.g., 10 or more, 12 or more, 15 or more, 18 or more, etc.) nucleotides, and that specifically bind to nucleic acids encoding one or more of the genes in Table 1. In some embodiments, the present invention provides an antibody that specifically binds to one or more of the genes in Table 1.

Embodiments of the present invention provide complexes of two or more nucleic acids or polypeptides described in table 1 with nucleic acid primers or probes or antibodies. In some embodiments, the present invention provides a multiplex (e.g., microarray) comprising reagents that binds to two or more nucleic acids or polypeptides described in Table 1.

EXPERIMENTAL

The following examples are provided in order to demonstrate and further illustrate certain preferred embodiments and aspects of the present invention and are not to be construed as limiting the scope thereof.

Example 1

Methods
Expression Microarray Data

Gene expression data of WT and NAMPT KD MCF-7 breast cancer cells (GSE13449) (Zhang, T. et al., *J Biol Chem* 284, 20408-20417, (2009)) and of WT and NAMPT KD pulmonary microvascular endothelial cells (GSE34512) (Cheranova, D., et al., *Genes Cells* 17, 420-430, (2012)) were obtained from the NCBI GEO database (Edgar, R., Domrachev, M. & Lash, A. E. et al., *Nucleic Acids Res* 30, 207-210, (2002)). The gene expression data of paired normal and tumor tissues for lung (GSE18842) (Sanchez-Palencia, A. et al. *Int J Cancer* 129, 355-364, (2011)), colon (GSE23878) (Uddin, S. et al. *Am J Pathol* 178, 537-547, (2011)), pancreatic (GSE15471) (Badea, L., et al., *Hepatogastroenterology* 55, 2016-2027, (2008)), and thyroid (GSE33630) cancers were also collected from the GEO database. Training and validation cohorts were constructed for lung and breast cancers. From the GEO database, the expression datasets with available information on recurrence-free survival were collected for lung (GSE8894 (Lee, E. S. et al. *Clinical cancer research: an official journal of the American Association for Cancer Research* 14, 7397-7404, (2008)) for training and GSE31210 (Okayama, H. et al. *Cancer Res* 72, 100-111, (2012)) and GSE37745 (Botling, J. et al. *Clinical cancer research: an official journal of the American Association for Cancer Research* 19, 194-204, (2013)) for validation) and breast (GSE2034 (Wang, Y. et al. *Lancet* 365, 671-679, (2005)) for training and GSE25066 (Hatzis, C. et al. *JAMA* 305, 1873-1881, (2011)) and GSE21653 (Sabatier, R. et al. *Breast Cancer Res Treat* 126, 407-420, (2011)) for validation) cancers.

Microarray Data Processing

The GC robust multichip average algorithm (Wu, Z. J., et al., *Journal of the American Statistical Association* 99, 909-917, (2004)) was used to summarize the expression level of each probe set for the microarray data of WT and NAMPT KD human cells and of paired normal and tumor tissues. Only the probe sets present (determined by function "mas5calls" in the Bioconductor "affy" package (Gautier, L., et al., *Bioinformatics* 20, 307-315, (2004))) in at least two thirds of the samples were retained. Analysis was restricted to the probe sets with unique annotations and removed genes on chromosomes X and Y to avoid potential confounding factors. Significance analysis of microarrays (Tusher, V. G., et al., *Proceedings of the National Academy of Sciences of the United States of America* 98, 5116-5121, (2001)), implemented in the samr library of the R Statistical Package, was used to compare $\log_2$-transformed gene expression levels between WT and NAMPT KD human cells. FDR was controlled using the q-value method (Storey, J. D. *Journal of the Royal Statistical Society Series B-Statistical Methodology* 64, 479-498, (2002); Taylor, J., et al., *Biostatistics* 6, 111-117, (2005)). Transcripts with a fold-change greater than 1.1 and FDR less than 0.05 were deemed differentially expressed.

Risk Scoring System

For each training cohort, univariate Cox proportional hazards regression was used to evaluate the association between recurrence-free survival and gene expression. A risk score was then calculated for each patient using a linear combination of gene expression weighted by the Wald statistic (ratio of regression coefficient to its standard error) as shown below:

$$S = \sum_{i=1}^{n} Z_i (e_i - \mu_i) / \tau_i$$

Here, S is the risk score of patient; n is the number of genes; $Z_i$ denotes the Wald statistic of gene i; $e_i$ denotes the expression level of gene i; and $\mu_i$ and $\tau_i$ are the mean and standard deviation of the gene expression values for gene i across all samples, respectively. Patients were then divided into positive and negative groups with the median of the risk score as the threshold. A higher risk score implies a poor outcome. The scoring system and the associated scaling coefficients were fixed based on the training cohorts and then evaluated in the validation cohorts. All statistical analyses were conducted using the R platform (version 2.15.1). The $\alpha$ level for all the statistical tests was 0.05.

Results

NAMPT-influenced Genes

The gene expression pattern between wild type and NAMPT-silenced human cells was compared to identify the genes regulated by NAMPT. Two independent microarray datasets containing gene expression information for both wild type and NAMPT-silenced cells were collected from the Gene Expression Omnibus (GEO) database (Edgar, R., et al., *Nucleic Acids Res* 30, 207-210, (2002)): one dataset was derived from a MCF-7 breast cancer cell line (GSE13449) (Zhang, T. et al. *J Biol Chem* 284, 20408-20417, (2009)) and the second dataset from human pulmonary microvascular endothelial cells (GSE34512) (Zhang, T. et al. *J Biol Chem* 284, 20408-20417, (2009)). The genes differentially expressed between WT and NAMPT KD cells in both datasets with accordant direction were retained as NAMPT-influenced genes. At the specified significance level of false discovery rate (FDR) <5% and fold change >1.1 (see Methods for details), 462 genes were found be commonly differentially expressed between WT and NAMPT KD cells, among which 361 genes were up-regulated while 101 genes were down-regulated in NAMPT KD cells (Table 2). The enriched Kyoto Encyclopedia of Genes and Genomes (KEGG) (Kanehisa, M., et al., *Nucleic Acids Res* 32, D277-280, (2004)) physiological pathways were searched among the dysregulated genes, revealing genes enriched in cancer-related KEGG terms, such as "Pathways in cancer", "Colorectal cancer", "Melanogenesis", "Renal cell carcinoma", and "Apoptosis" (FIG. 1, Fisher's exact test). These findings indicated that the NAMPT-influenced genes are involved in human cancer pathology.

Figure 2:
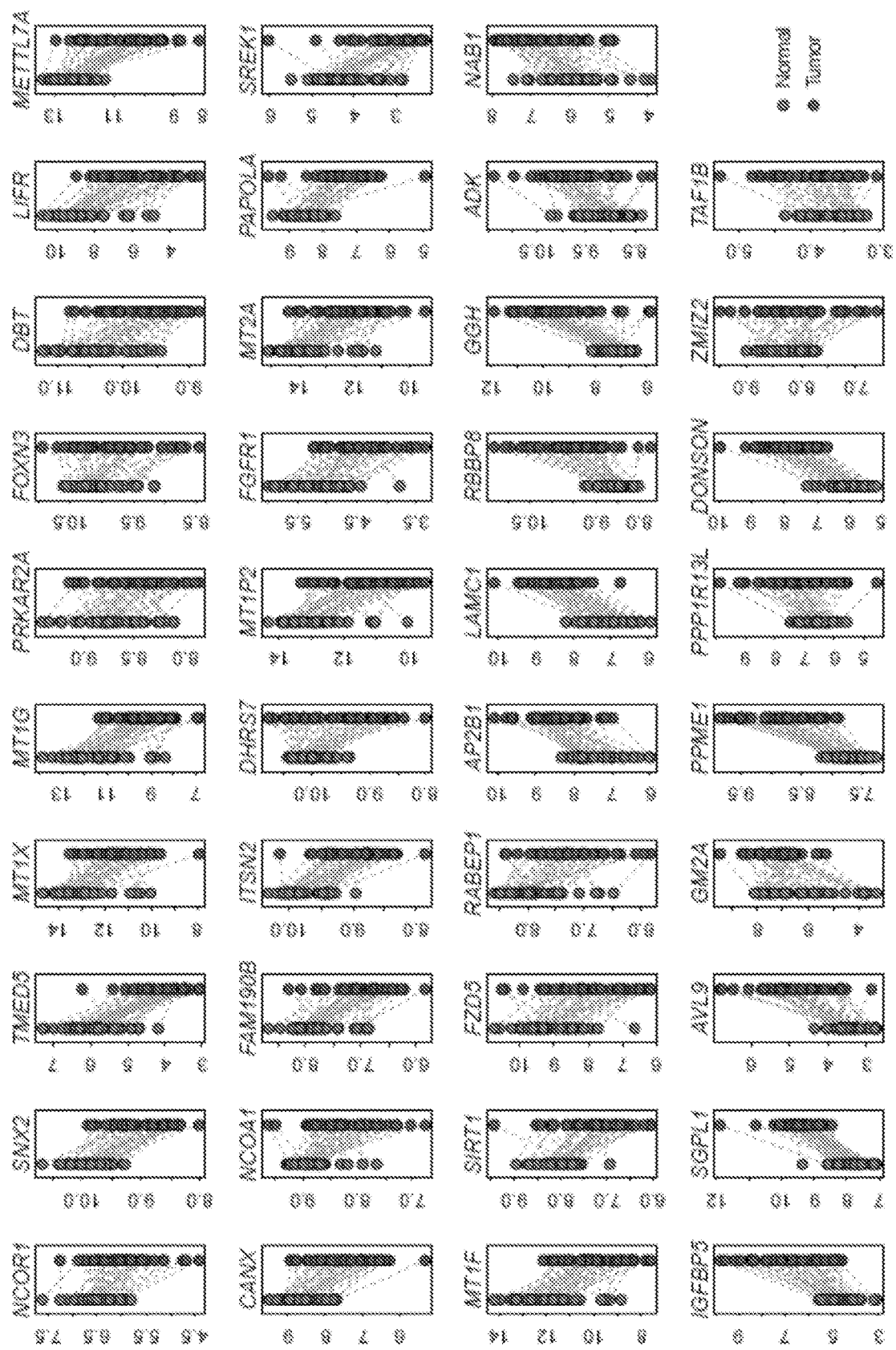
FIG. 2 shows a comparison of N39 gene expression between normal and lung cancer tissues.
Figure 6:
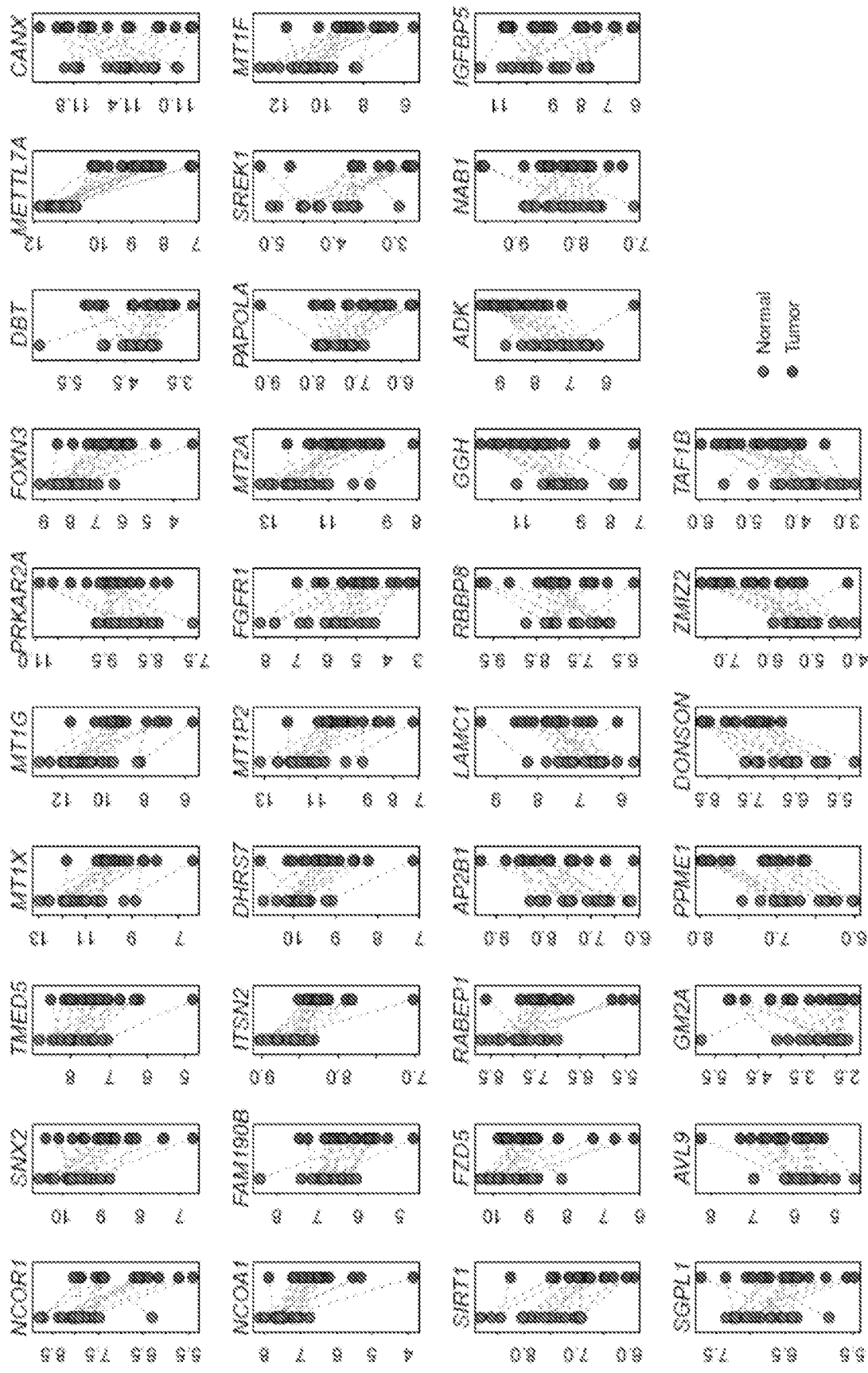
FIG. 6 shows a comparison of N39 gene expression between normal and tumor tissues in colon cancer.
Figure 7:
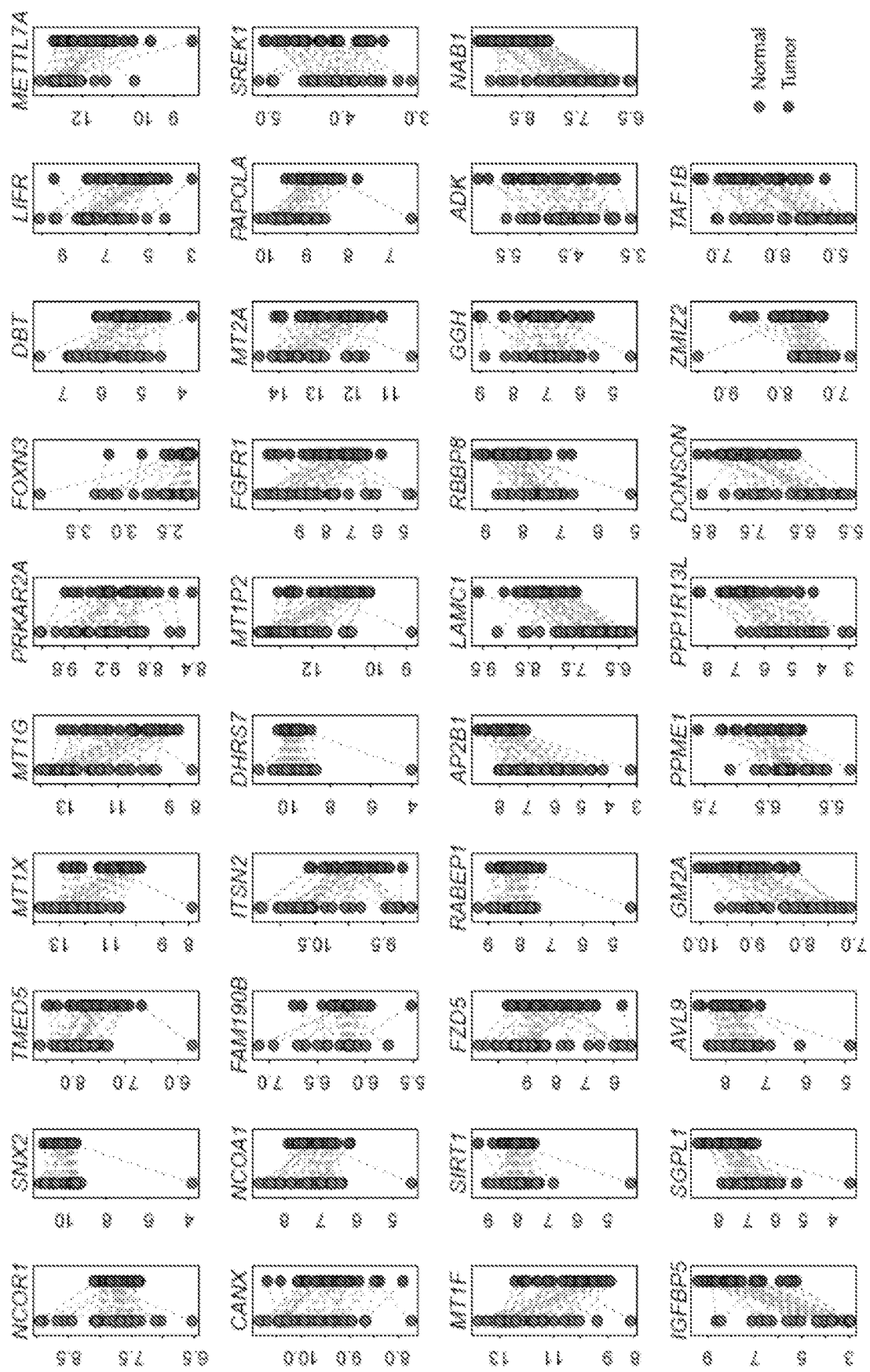
FIG. 7 shows a comparison of N39 gene expression between normal and tumor tissues in pancreatic cancer.

To determine the depth of involvement of NAMPT-influenced genes in human cancers, the difference in expression of these genes between normal and tumor tissues from lung (GSE18842) (Sanchez-Palencia, A. et al. *Int J Cancer* 129, 355-364, (2011)), colon (GSE23878) (Uddin, S. et al. *Am J Pathol* 178, 537-547, (2011)), pancreatic (GSE15471) (Badea, L., et al., *Hepatogastroenterology* 55, 2016-2027, (2008)), and thyroid (GSE33630) cancers was investigated. Paired normal and tumor tissues from 44 lung, 19 colon, 36 pancreatic, and 44 thyroid cancer patients were included. Paired t-test was used to detect the differentially expressed genes between the normal and tumor tissues. In total, 39 genes were identified as being mutually differentially expressed and concordant in expression with the NAMPT KD model (P<0.05 after Benjamini-Hochberg adjustment) in at least three out of four cancer types: lung cancer (FIG. 2), colon cancer (FIG. 6), pancreatic cancer (FIG. 7), and thyroid cancer (FIG. 7). This NAMPT-influenced 39-gene set was designated as the N39 gene signature (Table 1).

N39 Predicts Recurrence-free Survival in Lung and Breast Cancers

Figure 8:
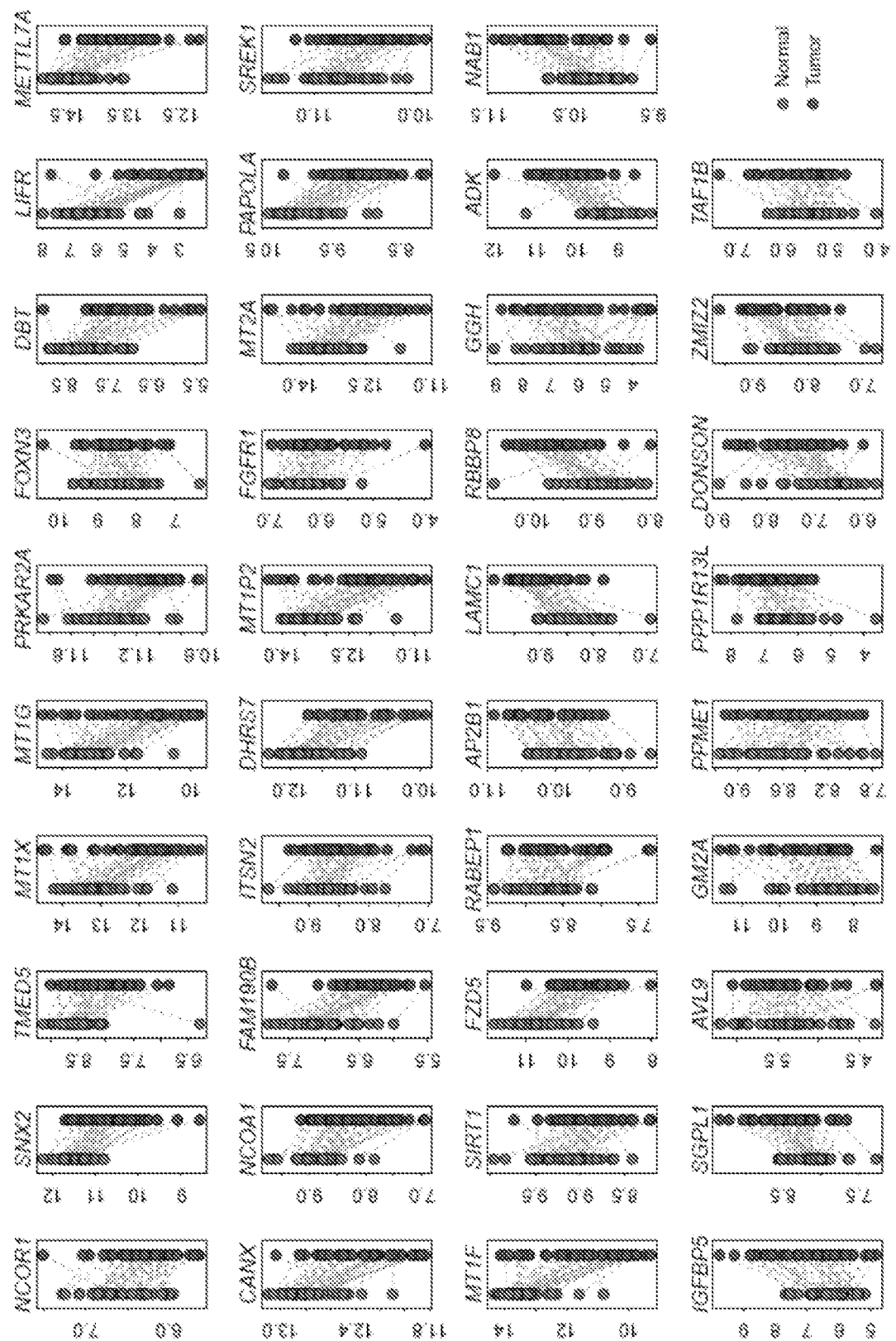
FIG. 8 shows a comparison of N39 gene expression between normal and tumor tissues in thyroid cancer.
Figure 9:
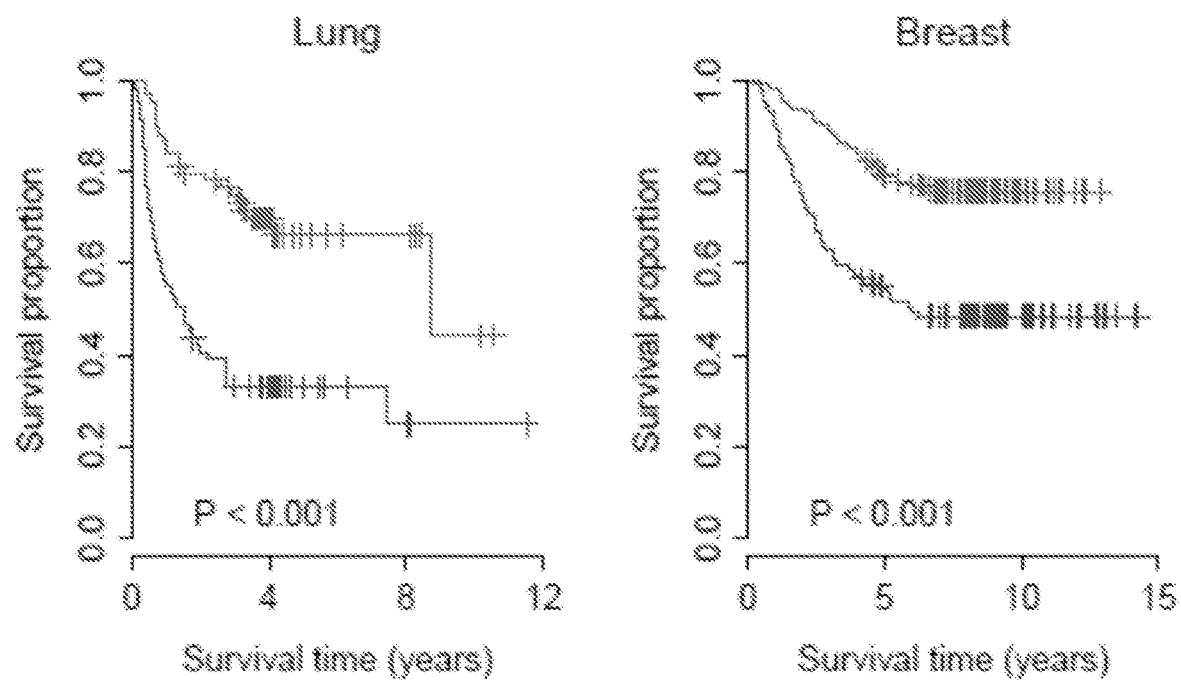
FIG. 9 shows Kaplan-Meier curves for patients in training cohorts.

A scoring system was constructed to assign each patient a risk score, representing a linear combination of the N39 gene expression values weighted by the coefficients obtained from training cohorts (GSE8894 (Lee, E. S. et al. *Clinical cancer research: an official journal of the American Association for Cancer Research* 14, 7397-7404, (2008)) for lung cancer and GSE2034 (Wang, Y. et al. *Lancet* 365, 671-679, (2005)) for breast cancer) (see Methods for details). N39-positive patients were defined as those having risk scores greater than the group median. There was a significantly reduced recurrence-free survival for N39-positive patients in the training cohorts (FIG. 8 and Table 4).

Figure 3:
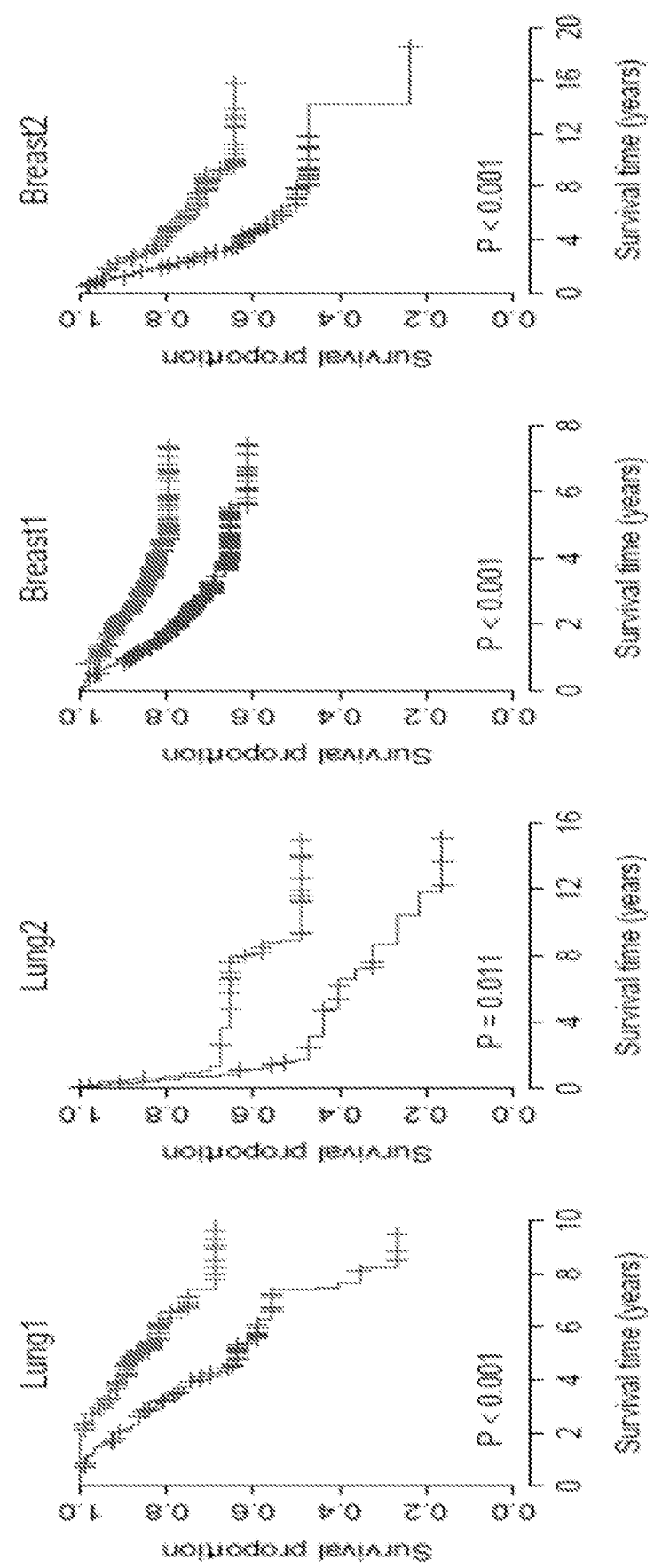
FIG. 3 shows Kaplan-Meier curves for patients in validation cohorts. The expression of N39 predicts poor recurrence-free survival in lung (Lung1 and Lung2 cohorts).

The ability of the N39 based risk score to classify patients into prognostic groups in independent validation cohorts was tested. For each cancer type, two validation cohorts were collected: Lung1 (GSE31210) (Okayama, H. et al. *Cancer Res* 72, 100-111, (2012)) and Lung2 (GSE37745) (Botling, J. et al. *Clinical cancer research: an official journal of the American Association for Cancer Research* 19, 194-204, (2013)) for lung cancer, and Breast1 (GSE25066) (Hatzis, C. et al. *JAMA* 305, 1873-1881, (2011)) and Breast2 (GSE21653) (Sabatier, R. et al. *Breast Cancer Res Treat* 126, 407-420, (2011)) for breast cancer. Kaplan-Meier survival curves demonstrated a significantly reduced recurrence-free survival for N39-positive patients in the validation cohorts (log-rank test: $P=5.4\times10^{-5}$ for Lung1; $P=0.011$ for Lung2; $P=2.9\times10^{-5}$ for Breast1; and $P=7.2\times10^{-4}$ for Breast2) (FIG. 3). Univariate Cox proportional hazards regression indicated that N39-positive patients exhibited significantly increased risk for recurrence (fold increase or FI) in these 4 cohorts: 2.88-FI for Lung1, 2.08-FI for Lung2, 2.27-FI for Breast1, and 2.12-FI for Breast2 (Table 2). These findings collectively indicate that N39 is predictive of recurrence-free survival in lung and breast cancer.

Figure 4:
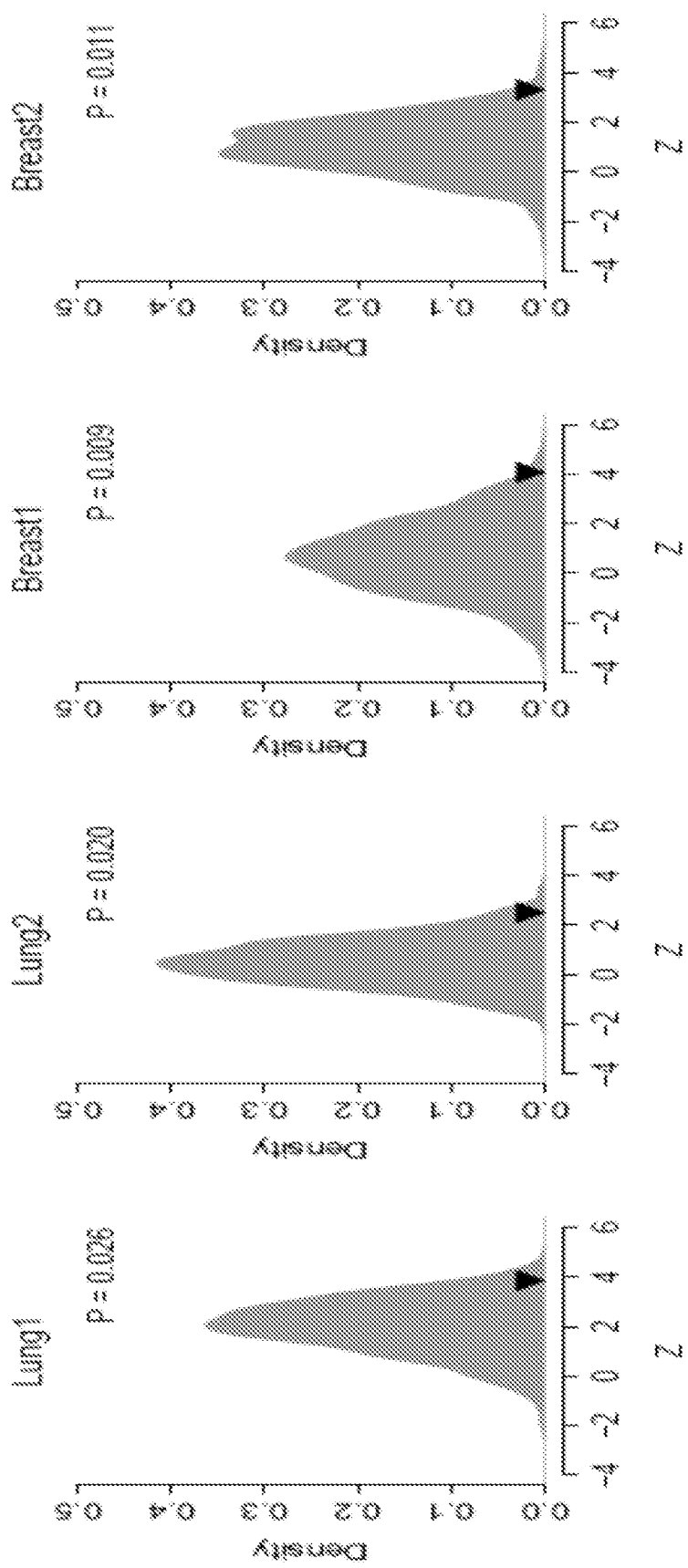
FIG. 4 shows non-random prognostic power of N39 in lung and breast cancers. Z denotes the Wald statistic, the ratio of Cox regression coefficient to its standard error. The black triangles stand for the Z values of N39. The grey areas show the distributions of Z values for the 1,000 resampled gene signatures with identical size as N39 under the null hypothesis of no association between N39 and recurrence-free survival.

In a recent computational study, 47 published breast cancer prognostic signatures were compared with signatures comprised of randomly selected genes. Approximately 60% of the published signatures were not significantly better than random signatures of identical size with the majority of random gene signatures significantly associated with breast cancer outcome (Venet, D., et al., *PLoS Comput Biol* 7, e1002240, (2011)). A resampling test was performed to determine whether the prognostic power of N39 was significantly better than random gene signatures. 1,000 random gene signatures of identical size as N39 (39 genes) were constructed with Cox proportional hazards regression of survival conducted for each resampled gene signature. The association between each random gene signature and recurrence-free survival was measured by the Wald statistic, the ratio of Cox regression coefficient to its standard error. It was contemplated that the Wald statistic value of N39 should be higher than that of randomized gene signatures if N39 was more predictive than randomized signatures. FIG. 4 indicates that the Wald statistic of N39 was significantly higher than that of randomized gene signatures (Right-tailed: $P=0.026$ for Lung1; $P=0.020$ for Lung2; $P=0.009$ for Breast1; and $P=0.011$ for Breast2), indicating that the null hypothesis that the association between N39 and recurrence-free survival is by chance is rejected.

N39 is Independent of Standard Clinical and Pathological Prognostic Factors

The performance of the N39 signature was investigated in comparison with standard clinical and pathological factors associated with prognosis in human cancers. For the Lung1 cohort, factors including patient age, gender, smoking history, stage, EGFR/KRAS/ALK gene alteration status, and MYC protein levels were compared. For the Lung2 cohort, age, gender, and stage were compared. For the Breast1 cohort, age, lymph node status, histological grade, tumor size, estrogen receptor (ER) status, and progesterone receptor (PR) status were compared. For the Breast2 cohort, factors such as age, grade, ER and PR status, and TP53 gene alteration status were included in the multivariate model. A multivariate Cox proportional hazards regression of survival indicated that N39 status remained a significant covariate in relation to the clinico-pathological factors in each validation cohorts ($P=1.2\times10^{-3}$ for Lung1; $P=6.4\times10^{-3}$ for Lung2; $P=2.9\times10^{-3}$ for Breast1; and $P=1.7\times10^{-2}$ for Breast2) (Table 3).

In the Lung2 and Breast2 cohorts, N39 status was the only significant covariate in the multivariate model (Table 3). However, in the Lung1 cohort, patient age, stage, and EGFR/KRAS/ALK alteration status were also significant variables. Therefore, the patients in the Lung1 cohort were further stratified according to respective significant factors and redid Cox proportional hazards regression. For patients aged <60 and ≥60, N39-positive patients had significant increased risk for recurrence, 2.62-FI (P=0.038) and 2.57-FI (P=0.005), respectively. For patients with stage I cancer (Lung1 cohort only includes patients with stage I and II lung cancer), N39-positive patients exhibited significantly increased risk for recurrence (2.48-FI, P=0.012), however, no significant difference was observed between N39-positive and -negative groups for patients with stage II lung cancer. For patients without and with EGFR/KRAS/ALK alteration, N39-positive patients had a 2.35-FI (P=0.041) and 2.36-FI (P=0.015) increased risk for recurrence, respectively. The performance of the N39 signature was investigated in patients without and with smoking history respectively and found N39-positive patients exhibited increased risk for recurrence in never-smokers and ever-smokers, 2.72-FI (P=0.012) and 2.19-FI (P=0.034) respectively. Kaplan-Meier survival curves demonstrated significantly reduced survival for N39-positive patients in each subset grouped by age, stage, EGFR/KRAS/ALK alteration status, and smoking history, with the exception of patients with stage II lung cancer (FIG. 5A), reflecting the reduced sample size.

Figure 5:
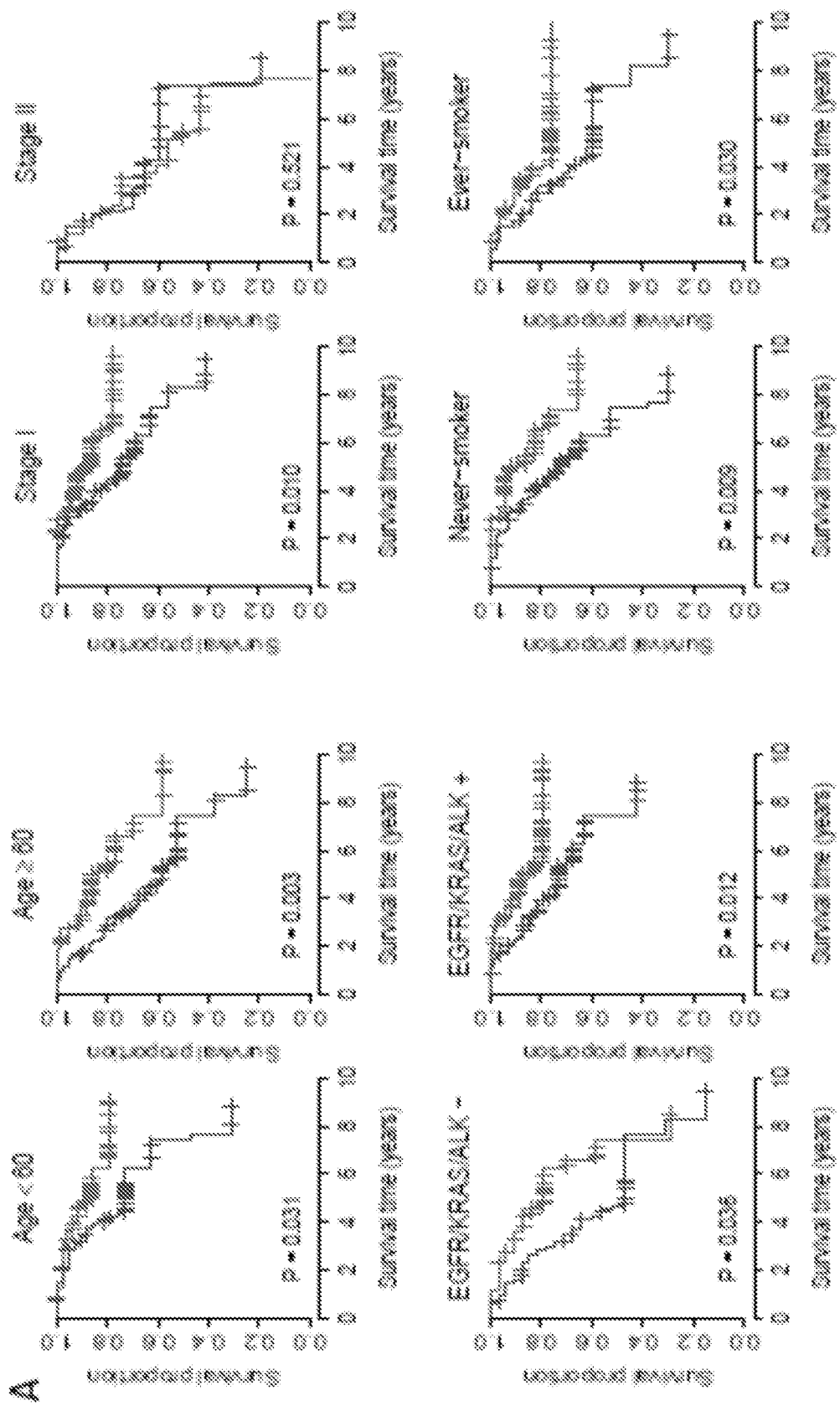
FIG. 5 shows Kaplan-Meier curves of patient cohorts grouped by clinical and pathological factors. (A) N39 is independent of traditional clinicopathological factors in lung cancer. (B) N39 is independent of traditional clinicopathological factors in breast cancer.
Figure 5:
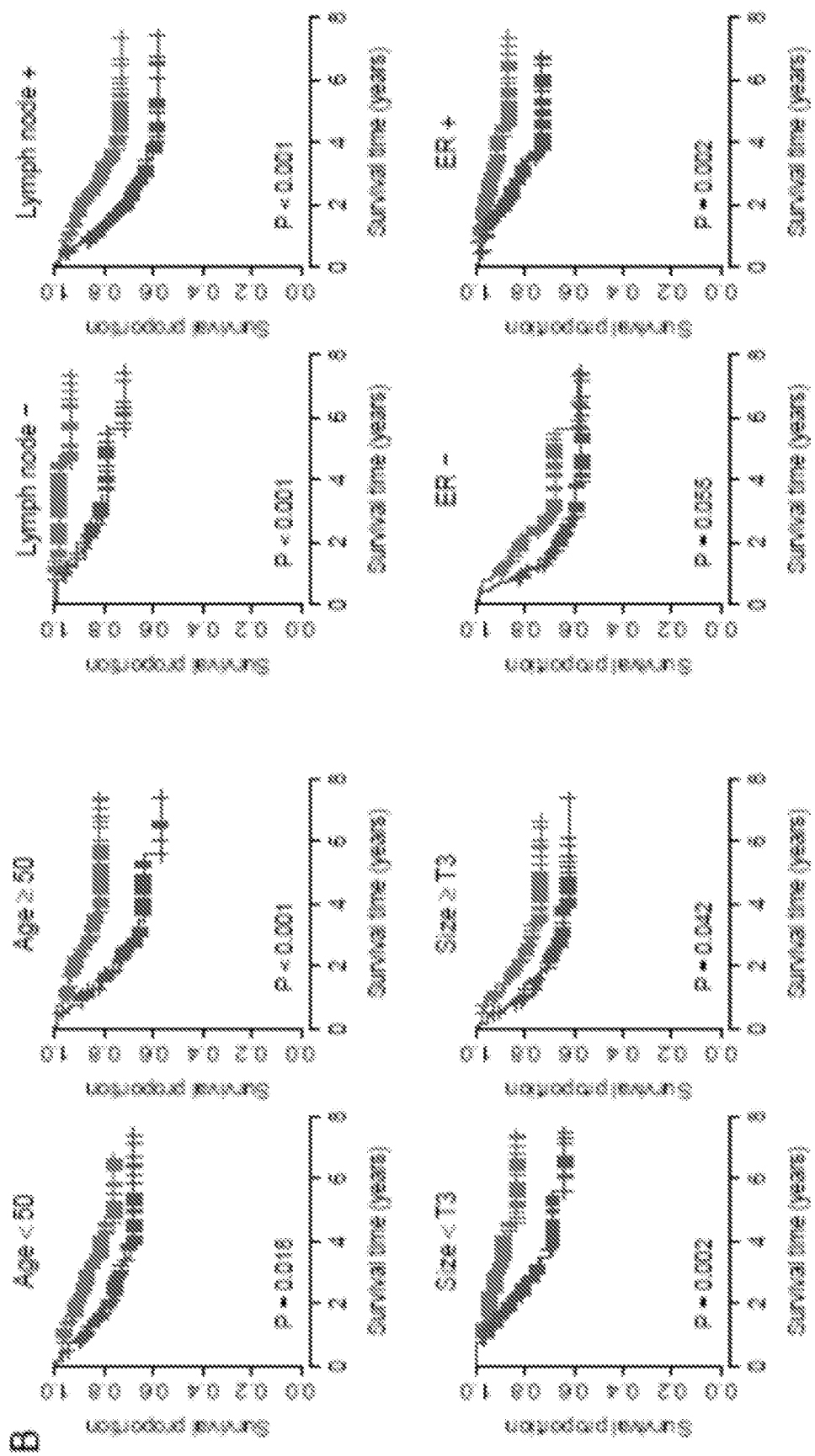

In the Breast1 cohort, lymph node status, tumor size, and ER status were significant clinicopathological factors in addition to N39 status (Table 3). Patients in the Breast1 cohort were stratified according to these factors. For patients with and without lymph node involvement, N39-positive patients exhibited significantly increased risk for recurrence, 8.03-FI (P=0.006) and 2.09-FI (P=$6.1 \times 10^{-4}$), respectively. For patients with tumor size <T3 and ≥T3, N39-positive patients displayed significant increased risk for recurrence, 2.56-FI (P=0.002) and 1.69-FI (P=0.044), respectively. For patients with ER negative status, N39-positive patients had a marginally increased risk for recurrence (1.59-FI, P=0.057), while for the ER positive group, N39-positive patients exhibited significantly increased risk for recurrence, 2.7-FI (P=0.004). Breast cancer is strongly related to age with ~80% of breast cancer occurring in women age >50. IT was demonstrated that N39-positive women age <50 exhibit a 1.9-FI (P=0.020) whereas women age >50 exhibit a 2.64-FI increased risk for recurrence (P=$8.4 \times 10^{-4}$). Kaplan-Meier survival curves confirmed a significantly reduced survival for N39-positive patients in each subset grouped by age, lymph node status, tumor size, and ER status (FIG. 5B).

The prognostic power with the gene sets regulated by NAMPT was investigated. Firstly, the critical role of NAMPT in carcinogenesis was confirmed by the gene ontology analysis of all NAMPT-mediated genes: eight of the eleven significantly deregulated pathways are direct cancer pathways (FIG. 1). Secondly, the N39 signature was generated by filtering through gene express data sets of four cancer types. Thirdly, the N39 signature was validated is a powerful tool to prognosticate lung and breast cancer and determined the N39 gene signature is a significant and independent predictor of cancer recurrence-free survival.

Lung and breast cancers were used as the validation study for cancer survival prognosis, mainly dependent on the availability of the datasets (three independent studies to serve as one discovery cohort and two validation cohorts). Moreover, this choice of cancer type selection is based on the severity of the two types of cancer. Lung cancer is the most frequently diagnosed cancers and leading cause of cancer death in males, comprising 17% of the total new cancer cases and 23% of the total cancer deaths (Jemal, A. et al. Global cancer statistics. *CA Cancer J Clin* 61, 69-90, (2011)). In females, breast cancer is the most frequently diagnosed cancer and the leading cause of cancer death, accounting for 23% of the total cancer cases and 14% of the cancer deaths (Jemal et al., supra).

Figure 10:
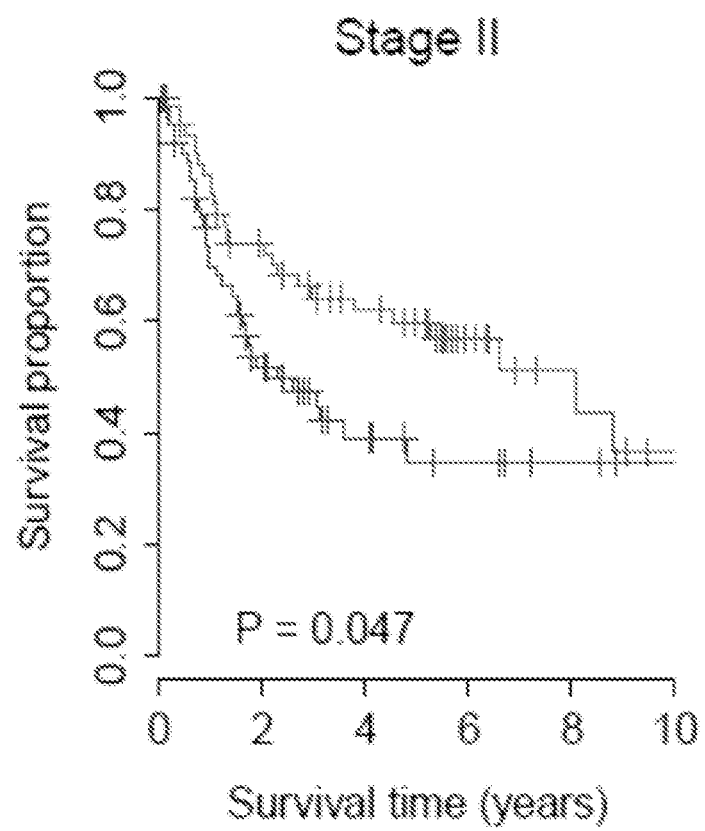
FIG. 10 shows Kaplan-Meier curves for lung cancer patients with stage II tumor.

Prognostic molecular signatures that work cooperatively with traditional clinical and pathological factors increase prognostic accuracy when identifying patients at higher risk for recurrence and death (Ko, J. H. et al. *Mol Cancer* 12, 106, (2013); Ko, J. H. et al. *PLoS One* 9, e86569, (2014); Pitroda, S. P. et al. *PLoS One* 7, e46104, (2012)). The molecular signature that is composed of 39 NAMPT-mediated genes is a strong prognostic marker, because N39 was solely developed based on the discovery cohort and its prognostic power was validated in two independent validation cohorts for lung and breast cancer, respectively. N39 was independent of other clinicopathological covariates. In the Lung1 cohort, when grouped by age, EGFR/KRAS/ALK alteration status, and smoking history, N39 further stratified lung cancer patients with significant differences in survival. A significantly increased risk of recurrence was also observed in N39-positive patients of stage I. To validate the prognostic power of N39 in stage II tumor, an additional lung cancer dataset (GSE41271) (Sato, M. et al. *Molecular cancer research: MCR* 11, 638-650, (2013)) was included here. The subjects of stage II were merged from three independent cohorts (Lung1, Lung2, and GSE41271) using the "metaArray" package in Bioconductor (see FIG. 10 for details). It was found that N39-positive patients (with stage II tumor) exhibited a significantly increased risk (1.68-FI, P=0.049 by univariate Cox proportional hazards regression) for recurrence comparing with N39-negative patients. Also, Kaplan-Meier survival curves confirmed a significantly reduced survival (P=0.047 by log-rank test) for N39-positive patients of stage II (FIG. 10). In the Breast1 cohort, patients were stratified according to age, lymph node status, tumor size, and ER status, respectively. A significantly increased risk of recurrence was also observed in N39-positive patients in each category, except for the marginal signal in ER negative patients. Taken together, these results confirm that N39 is not dependent on specific values of the respective covariates status, which enhances the identification of cancer patients at greater risk for recurrence.

Figure 11:
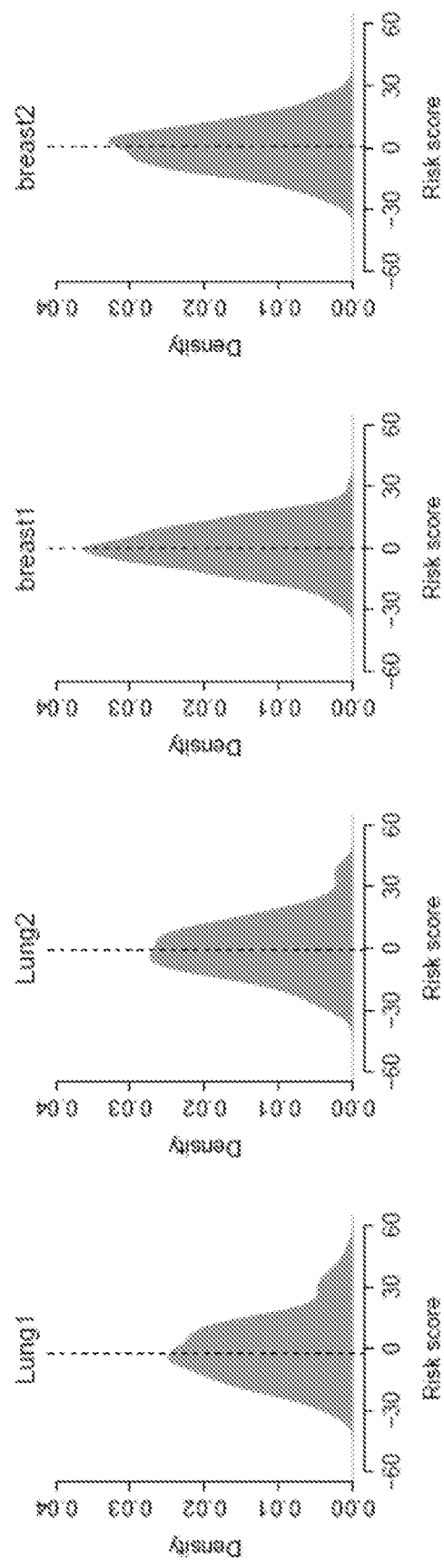
FIG. 11 shows distribution of N39 risk score in validation cohorts. The vertical dash line indicates the median of risk score.

The median of N39 risk score was used as a cutoff to stratify patents into two groups (N39-positive and -negative) to conduct categorized statistical analyses (such as Kaplan-Meier analysis and log-rank test), although other cut-off scores may be utilized. Clinically, zero can be utilized as an absolute cutoff to divide patients into high- and low-risk groups, as the median of N39 score is approximately equal to zero in each validation cohort (FIG. 11).

In addition to its prognosis utility, N39 gene list also provides a set of NAMPT associated genes that play critical roles in cancer pathogenesis. One good example is SIRT1. NAMPT-SIRT1-MYC axis critically regulates cell survival (Menssen, A. et al. *Proceedings of the National Academy of Sciences of the United States of America* 109, E187-196, (2012)). SIRT1 is also found over-expressed in many cancers and frequently NAMPT is concurrently over-expressed with SIRT1, which is important for prostate cancer cell survival and stress response (Wang, Z. et al. *Oncogene* 32, 589-598, (2013)). A recent study in pancreatic cancer lines, however, indicated that NADase CD38 but not SIRT1 is crucial for pancreatic cancer cells' response to NAMPT inhibition (Chini, C. C. et al. *Clinical cancer research: an*

*official journal of the American Association for Cancer Research* 20, 120-130, (2014)), indicating the complex interaction of NAMPT with SIRT1. These previous findings, together with N39 signature, have generated novel biomarkers and therapeutic targets in cancer.

TABLE 1

N39 gene set

| Gene symbol | Gene title |
|---|---|
| ADK | adenosine kinase |
| AP2B1 | adaptor-related protein complex 2, beta 1 subunit |
| AVL9 | AVL9 homolog (*S. cerevisiae*) |
| CANX | calnexin |
| DBT | dihydrolipoamide branched chain transacylase E2 |
| DHRS7 | dehydrogenase/reductase (SDR family) member 7 |
| DONSON | downstream neighbor of SON |
| FAM190B | family with sequence similarity 190, member B |
| FGFR1 | fibroblast growth factor receptor 1 |
| FOXN3 | forkhead box N3 |
| FZD5 | frizzled family receptor 5 |
| GGH | gamma-glutamyl hydrolase (conjugase, folylpolygammaglutamyl hydrolase) |
| GM2A | GM2 ganglioside activator |
| IGFBP5 | insulin-like growth factor binding protein 5 |
| ITSN2 | intersectin 2 |
| LAMC1 | laminin, gamma 1 (formerly LAMB2) |
| LIFR | leukemia inhibitory factor receptor alpha |
| METTL7A | methyltransferase like 7A |
| MT1F | metallothionein 1F |
| MT1G | metallothionein 1G |
| MT1P2 | metallothionein 1 pseudogene 2 |
| MT1X | metallothionein 1X |
| MT2A | metallothionein 2A |
| NAB1 | NGFI-A binding protein 1 (EGR1 binding protein 1) |
| NCOA1 | nuclear receptor coactivator 1 |
| NCOR1 | nuclear receptor corepressor 1 |
| PAPOLA | poly(A) polymerase alpha |
| PPME1 | protein phosphatase methylesterase 1 |
| PPP1R13L | protein phosphatase 1, regulatory subunit 13 like |
| PRKAR2A | protein kinase, cAMP-dependent, regulatory, type II, alpha |
| RABEP1 | rabaptin, RAB GTPase binding effector protein 1 |
| RBBP8 | retinoblastoma binding protein 8 |
| SGPL1 | sphingosine-1-phosphate lyase 1 |
| SIRT1 | sirtuin 1 |
| SNX2 | sorting nexin 2 |
| SREK1 | splicing regulatory glutamine/lysine-rich protein 1 |
| TAF1B | TATA box binding protein (TBP)-associated factor, RNA polymerase I, B, 63 kDa |
| TMED5 | transmembrane emp24 protein transport domain containing 5 |
| ZMIZ2 | zinc finger, MIZ-type containing 2 |

TABLE 2

Cox proportional hazards regression of survival by N39 status in lung and breast cancers

| | Training cohort | | | | Validation cohort | | | | |
|---|---|---|---|---|---|---|---|---|---|
| Cancer | n | HR | 95% CI | P-value | Cohort | n | HR | 95% CI | P-value |
| Lung | 138 | 3.18 | (1.91, 5.29) | $8.4 \times 10^{-6}$ | Lung1 | 226 | 2.88 | (1.69, 4.95) | $1.2 \times 10^{-4}$ |
| | | | | | Lung2 | 96 | 2.08 | (1.17, 3.70) | $1.3 \times 10^{-2}$ |
| Breast | 286 | 2.76 | (1.83, 4.14) | $1.1 \times 10^{-6}$ | Breast1 | 508 | 2.27 | (1.53, 3.37) | $4.8 \times 10^{-5}$ |
| | | | | | Breast2 | 252 | 2.12 | (1.36, 3.30) | $9.5 \times 10^{-4}$ |

Note n: sample size;

HR: hazard ratio;

CI: confidence interval

TABLE 3

Multivariate Cox proportional hazards regression of survival in the validation cohorts

| Cohort | Covariate | HR | 95% CI | P-value |
|---|---|---|---|---|
| Lung1 | N39 + vs. − | 2.51 | (1.44, 4.37) | $1.2 \times 10^{-3}$ |
| | Age (per year) | 1.04 | (1.00, 1.08) | $2.9 \times 10^{-2}$ |
| | Gender male vs. female | 0.70 | (0.35, 1.41) | $3.2 \times 10^{-1}$ |
| | Smoking + vs. − | 1.40 | (0.72, 2.75) | $3.2 \times 10^{-1}$ |
| | Stage | 2.86 | (1.68, 4.85) | $9.8 \times 10^{-5}$ |
| | EGFR/KRAS/ALK alteration + vs. − | 0.57 | (0.34, 0.96) | $3.6 \times 10^{-2}$ |
| | MYC level high vs. low | 0.90 | (0.35, 2.32) | $8.3 \times 10^{-1}$ |
| Lung2 | N39 + vs. − | 2.32 | (1.27, 4.25) | $6.4 \times 10^{-3}$ |
| | Age (per year) | 1.00 | (0.97, 1.04) | $8.0 \times 10^{-1}$ |
| | Gender male vs. female | 0.85 | (0.47, 1.54) | $5.9 \times 10^{-1}$ |
| | Stage | 1.44 | (0.99, 2.09) | $5.5 \times 10^{-2}$ |
| Breast1 | N39 + vs. − | 1.97 | (1.26, 3.07) | $2.9 \times 10^{-3}$ |
| | Age (per year) | 1.00 | (0.98, 1.02) | $9.6 \times 10^{-1}$ |
| | Lymph node + vs. − | 2.88 | (1.66, 5.00) | $1.8 \times 10^{-4}$ |
| | Grade 3 vs. 1, 2 | 0.73 | (0.45, 1.18) | $2.0 \times 10^{-1}$ |
| | Tumor size ≥T3 vs. <T3 | 1.65 | (1.11, 2.46) | $1.3 \times 10^{-2}$ |
| | ER + vs. − | 0.52 | (0.30, 0.90) | $2.0 \times 10^{-2}$ |
| | PR + vs. − | 0.66 | (0.39, 1.14) | $1.4 \times 10^{-1}$ |
| Breast2 | N39 + vs. − | 1.97 | (1.13, 3.43) | $1.7 \times 10^{-2}$ |
| | Age (per year) | 1.00 | (0.98, 1.02) | $8.5 \times 10^{-1}$ |
| | Grade 3 vs. 1, 2 | 0.92 | (0.52, 1.63) | $7.7 \times 10^{-1}$ |
| | ER + vs. − | 0.70 | (0.26, 1.86) | $4.7 \times 10^{-1}$ |
| | PR + vs. − | 1.35 | (0.52, 3.50) | $5.4 \times 10^{-1}$ |
| | TP53 alteration + vs. − | 1.48 | (0.87, 2.51) | $1.4 \times 10^{-1}$ |

Note -

HR: hazard ratio;

CI: confidence interval

TABLE 4

| Gene symbol | Gene title | GSE13449 Fold change | GSE13449 FDR (%) | GSE34512 Fold change | GSE34512 FDR (%) |
|---|---|---|---|---|---|
| AASDHPPT | aminoadipate-semialdehyde dehydrogenase-phosphopantetheinyl transferase | 1.31 | 4.09 | 2.52 | 0.00 |
| ABAT | 4-aminobutyrate aminotransferase | 1.28 | 4.09 | 1.45 | 1.04 |
| ABCD3 | ATP-binding cassette, sub-family D (ALD), member 3 | 0.91 | 4.09 | 0.83 | 2.90 |
| ABCE1 | ATP-binding cassette, sub-family E (OABP), member 1 | 1.16 | 4.09 | 1.49 | 0.00 |
| ABHD10 | abhydrolase domain containing 10 | 0.89 | 4.09 | 0.75 | 2.90 |
| ABI2 | abl-interactor 2 | 0.84 | 0.00 | 0.81 | 3.72 |
| ACO1 | aconitase 1, soluble | 0.90 | 4.09 | 0.59 | 3.72 |
| ACSL3 | acyl-CoA synthetase long-chain family member 3 | 1.43 | 4.09 | 1.27 | 0.00 |
| ADAM17 | ADAM metallopeptidase domain 17 | 1.15 | 4.09 | 1.16 | 0.00 |
| ADK | adenosine kinase | 0.81 | 0.00 | 0.78 | 3.72 |
| AGTPBP1 | ATP/GTP binding protein 1 | 0.81 | 4.09 | 0.69 | 2.90 |
| ALG9 | asparagine-linked glycosylation 9, alpha-1,2-mannosyltransferase homolog (S. cerevisiae) | 0.82 | 4.09 | 0.80 | 2.90 |
| ANAPC13 | anaphase promoting complex subunit 13 | 0.90 | 0.00 | 0.84 | 2.90 |
| ANKRD10 | ankyrin repeat domain 10 | 1.26 | 4.09 | 1.55 | 0.00 |
| ANKRD17 | ankyrin repeat domain 17 | 1.19 | 4.09 | 1.50 | 0.00 |
| ANKRD27 | ankyrin repeat domain 27 (VPS9 domain) | 1.13 | 4.09 | 1.27 | 0.00 |
| ANP32E | acidic (leucine-rich) nuclear phosphoprotein 32 family, member E | 1.48 | 4.09 | 1.14 | 1.04 |
| AP2B1 | adaptor-related protein complex 2, beta 1 subunit | 0.89 | 0.00 | 0.54 | 2.90 |
| AP4E1 | adaptor-related protein complex 4, epsilon 1 subunit | 1.20 | 4.09 | 1.50 | 0.00 |
| ARHGEF2 | Rho/Rac guanine nucleotide exchange factor (GEF) 2 | 1.55 | 4.09 | 1.89 | 0.00 |
| ARHGEF3 | Rho guanine nucleotide exchange factor (GEF) 3 | 1.33 | 4.09 | 1.39 | 0.00 |
| ARL6IP1 | ADP-ribosylation factor-like 6 interacting protein 1 | 1.18 | 4.09 | 1.74 | 0.00 |
| ASB8 | ankyrin repeat and SOCS box containing 8 | 0.90 | 0.00 | 0.52 | 2.90 |
| ASF1A | ASF1 anti-silencing function 1 homolog A (S. cerevisiae) | 1.21 | 4.09 | 1.44 | 0.00 |
| ASUN | asunder, spermatogenesis regulator homolog (Drosophila) | 1.21 | 4.09 | 1.78 | 0.00 |
| ATF7IP | activating transcription factor 7 interacting protein | 1.45 | 4.09 | 2.03 | 0.00 |
| ATP10D | ATPase, class V, type 10D | 0.77 | 4.09 | 0.76 | 2.90 |
| ATP2C1 | ATPase, Ca++ transporting, type 2C, member 1 | 1.24 | 4.09 | 1.49 | 0.00 |
| ATXN1 | ataxin 1 | 0.81 | 0.00 | 0.79 | 2.90 |
| ATXN10 | ataxin 10 | 2.24 | 4.09 | 1.38 | 0.00 |
| AVL9 | AVL9 homolog (S. cerevisiae) | 0.90 | 0.00 | 0.52 | 2.90 |
| AVPI1 | arginine, vasopressin-induced 1 | 1.24 | 4.09 | 1.34 | 1.04 |
| BAX | BCL2-associated X protein | 1.19 | 4.09 | 2.12 | 0.00 |
| BAZ1A | bromodomain adjacent to zinc finger domain, 1A | 1.38 | 4.09 | 1.24 | 0.00 |
| BAZ2A | bromodomain adjacent to zinc finger domain, 2A | 1.12 | 4.09 | 2.02 | 0.00 |
| BBX | bobby sox homolog (Drosophila) | 1.45 | 4.09 | 1.34 | 0.00 |
| BCAR3 | breast cancer anti-estrogen resistance 3 | 1.21 | 4.09 | 1.39 | 0.00 |
| BCAT1 | branched chain amino-acid transaminase 1, cytosolic | 1.21 | 4.09 | 1.30 | 1.04 |
| BLVRB | biliverdin reductase B (flavin reductase (NADPH)) | 1.20 | 4.09 | 1.74 | 0.00 |
| BMPR2 | bone morphogenetic protein receptor, type II (serine/threonine kinase) | 1.72 | 4.09 | 1.57 | 0.00 |
| BST2 | bone marrow stromal cell antigen 2 | 1.27 | 4.09 | 1.46 | 0.00 |
| BTBD7 | BTB (POZ) domain containing 7 | 0.81 | 0.00 | 0.88 | 2.90 |
| BTG3 | BTG family, member 3 | 0.67 | 0.00 | 0.75 | 2.90 |
| C10orf57 | chromosome 10 open reading frame 57 | 0.78 | 0.00 | 0.91 | 3.72 |
| C12orf29 | chromosome 12 open reading frame 29 | 0.89 | 0.00 | 0.82 | 2.90 |
| C12orf35 | chromosome 12 open reading frame 35 | 1.30 | 4.09 | 1.45 | 0.00 |
| C12orf51 | chromosome 12 open reading frame 51 | 1.12 | 4.09 | 1.64 | 0.00 |
| C1orf115 | chromosome 1 open reading frame 115 | 1.38 | 4.09 | 1.31 | 1.04 |
| C1orf63 | chromosome 1 open reading frame 63 | 1.16 | 4.09 | 1.69 | 0.00 |
| C21orf91 | chromosome 21 open reading frame 91 | 0.89 | 4.09 | 0.89 | 3.61 |
| CAND1 | cullin-associated and neddylation-dissociated 1 | 1.11 | 4.09 | 2.77 | 0.00 |
| CANX | calnexin | 1.19 | 4.09 | 1.24 | 0.00 |
| CAP2 | CAP, adenylate cyclase-associated protein, 2 (yeast) | 1.27 | 4.09 | 1.14 | 0.00 |
| CAPN1 | calpain 1, (nm/I) large subunit | 1.13 | 4.09 | 1.49 | 1.04 |
| CASP4 | caspase 4, apoptosis-related cysteine peptidase | 1.18 | 4.09 | 1.26 | 1.04 |
| CAST | calpastatin | 1.97 | 4.09 | 1.21 | 0.00 |
| CCDC47 | coiled-coil domain containing 47 | 1.40 | 4.09 | 1.14 | 0.00 |
| CCDC85C | coiled-coil domain containing 85C | 1.11 | 4.09 | 1.27 | 1.04 |
| CCNB1 | cyclin B1 | 1.21 | 4.09 | 1.68 | 0.00 |
| CCND1 | cyclin D1 | 1.19 | 4.09 | 1.45 | 0.00 |
| CD47 | CD47 molecule | 1.12 | 4.09 | 1.69 | 0.00 |
| CDK13 | cyclin-dependent kinase 13 | 1.23 | 4.09 | 1.45 | 0.00 |
| CDK14 | cyclin-dependent kinase 14 | 0.44 | 0.00 | 0.81 | 3.72 |
| CDKN2C | cyclin-dependent kinase inhibitor 2C (p18, inhibits CDK4) | 0.83 | 0.00 | 0.73 | 2.90 |
| CDV3 | CDV3 homolog (mouse) | 1.16 | 4.09 | 1.19 | 0.00 |
| CEP104 | centrosomal protein 104 kDa | 1.39 | 4.09 | 1.41 | 0.00 |
| CEP350 | centrosomal protein 350 kDa | 1.25 | 4.09 | 1.52 | 0.00 |
| CHKA | choline kinase alpha | 1.25 | 4.09 | 1.72 | 0.00 |
| CHMP1B | charged multivesicular body protein 1B | 0.83 | 0.00 | 0.85 | 3.72 |
| CKAP4 | cytoskeleton-associated protein 4 | 1.46 | 4.09 | 1.40 | 0.00 |

TABLE 4-continued

|  |  | GSE13449 | | GSE34512 | |
| --- | --- | --- | --- | --- | --- |
| Gene symbol | Gene title | Fold change | FDR (%) | Fold change | FDR (%) |
| CNOT4 | CCR4-NOT transcription complex, subunit 4 | 1.10 | 4.09 | 1.44 | 0.00 |
| COG7 | component of oligomeric golgi complex 7 | 1.13 | 4.09 | 1.40 | 1.04 |
| COQ10B | coenzyme Q10 homolog B (S. cerevisiae) | 1.27 | 4.09 | 1.23 | 0.00 |
| CPNE1 | copine I | 1.23 | 4.09 | 2.43 | 0.00 |
| CPNE3 | copine III | 1.11 | 4.09 | 1.29 | 0.00 |
| CREBL2 | cAMP responsive element binding protein-like 2 | 0.81 | 0.00 | 0.90 | 3.72 |
| CROT | carnitine O-octanoyltransferase | 1.14 | 4.09 | 1.33 | 0.00 |
| CSRP2 | cystiene and glycine-rich protein 2 | 0.61 | 0.00 | 0.80 | 3.72 |
| CTBP2 | C-terminal binding protein 2 | 1.16 | 4.09 | 1.14 | 0.00 |
| CTNNB1 | catenin (cadherin-associated protein), beta 1, 88 kDa | 1.11 | 4.09 | 1.25 | 0.00 |
| CTSC | cathepsin C | 0.46 | 0.00 | 0.81 | 2.90 |
| CUL2 | cullin 2 | 1.30 | 4.09 | 1.26 | 0.00 |
| CUL3 | cullin 3 | 1.10 | 4.09 | 1.27 | 0.00 |
| CXADR | coxsackie virus and adenovirus receptor | 0.77 | 4.09 | 0.62 | 2.90 |
| CXCL12 | chemokine (C-X-C motif) ligand 12 | 0.54 | 0.00 | 0.63 | 3.61 |
| CYBRD1 | cytochrome b reductase 1 | 0.80 | 4.09 | 0.70 | 2.90 |
| DBT | dihydrolipoamide branched chain transacylase E2 | 1.13 | 4.09 | 1.24 | 1.04 |
| DCLRE1C | DNA cross-link repair 1C | 1.19 | 4.09 | 1.35 | 0.00 |
| DDIT4 | DNA-damage-inducible transcript 4 | 1.54 | 4.09 | 1.62 | 0.00 |
| DDX18 | DEAD (Asp-Glu-Ala-Asp) box polypeptide 18 | 1.24 | 4.09 | 1.10 | 0.00 |
| DDX54 | DEAD (Asp-Glu-Ala-Asp) box pelypeptide 54 | 1.18 | 4.09 | 1.28 | 1.04 |
| DHRS7 | dehydrogenase/reductase (SDR family) member 7 | 1.30 | 4.09 | 1.43 | 0.00 |
| DHX29 | DEAH (Asp-Glu-Ala-His) box polypeptide 29 | 1.27 | 4.09 | 1.17 | 1.04 |
| DHX8 | DEAH (Asp-Glu-Ala-His) box polypeptide 8 | 0.84 | 0.00 | 0.90 | 3.72 |
| DIP2C | DIP2 disco-interacting protein 2 homolog C (Drosophila) | 1.28 | 4.09 | 1.72 | 0.00 |
| DLGAP4 | discs, large (Drosophila) homolog-associated protein 4 | 1.18 | 4.09 | 1.21 | 1.04 |
| DNAJA2 | DnaJ (Hsp40) homolog, subfamily A, member 2 | 1.15 | 4.09 | 1.40 | 0.00 |
| DNAJC2 | DnaJ (Hsp40) homolog, subfamily C, member 2 | 1.35 | 4.09 | 1.32 | 0.00 |
| DNTTIP2 | deoxynucleotidyltransferase, terminal interacting protein 2 | 1.22 | 4.09 | 1.18 | 1.04 |
| DOCK9 | dedicator of cytokinesis 9 | 1.14 | 4.09 | 1.12 | 0.00 |
| DONSON | downstream neighbor of SON | 0.73 | 0.00 | 0.80 | 2.90 |
| DPP8 | dipeptidyl-peptidase 8 | 1.18 | 4.09 | 1.35 | 0.00 |
| DRAM1 | DNA-damage regulated autophagy modulator 1 | 1.34 | 4.09 | 1.14 | 1.04 |
| DYRK2 | dual-specificity tyrosine-(Y)-phosphorylation regulated kinase 2 | 0.81 | 0.00 | 0.66 | 2.90 |
| EFEMP1 | EGF containing fibulin-like extracellular matrix proteain 1 | 1.23 | 4.09 | 1.18 | 3.24 |
| EFNA1 | ephrin-A1 | 0.91 | 0.00 | 0.82 | 2.90 |
| EIF2S1 | eukaryotic translation initiation factor 2, subunit 1 alpha, 35 kDa | 1.11 | 4.09 | 1.28 | 0.00 |
| EIF4E | eukaryotic translation initiation factor 4E | 1.15 | 4.09 | 2.09 | 0.00 |
| EIF4EBP2 | eukaryotic translation initiation factor 4E binding protein 2 | 0.85 | 0.00 | 0.87 | 3.72 |
| EIF4G1 | eukaryotic translation initiation factor 4 gamma, 1 | 1.13 | 4.09 | 1.56 | 1.04 |
| EIF5B | eukaryotic translation initiation factor 5B | 1.74 | 4.09 | 1.38 | 0.00 |
| ELOVL6 | ELOVL fatty acid elongase 6 | 1.23 | 4.09 | 1.13 | 1.04 |
| ENO1 | enolase 1, (alpha) | 1.13 | 4.09 | 1.34 | 0.00 |
| ENO2 | enolase 2 (gamma, neuronal) | 0.91 | 0.00 | 0.51 | 3.72 |
| ENSA | endosulfine alpha | 1.12 | 4.09 | 1.35 | 0.00 |
| EP300 | E1A binding protein p300 | 1.21 | 4.09 | 1.14 | 0.00 |
| EPHB4 | EPH receptor B4 | 1.38 | 4.09 | 1.91 | 0.00 |
| EPS15 | epidermal growth factor receptor pathway substrate 15 | 1.58 | 4.09 | 16.59 | 0.00 |
| EPS8 | epidermal growth factor receptor pathway substrate 8 | 0.86 | 0.00 | 0.67 | 2.90 |
| EXT1 | exostosin 1 | 0.69 | 0.00 | 0.56 | 2.90 |
| EZH2 | enhancer of zeste homolog 2 (Drosophila) | 0.83 | 4.09 | 0.41 | 2.90 |
| EZR | ezrin | 1.18 | 4.09 | 2.42 | 0.00 |
| FABP5 | fatty acid binding protein 5 (psoriasis-associated) | 1.21 | 4.09 | 1.19 | 0.00 |
| FAM134A | family with sequence similarity 134, member A | 0.74 | 0.00 | 0.88 | 3.72 |
| FAM172A | family with sequence similarity 172, member A | 0.76 | 0.00 | 0.68 | 2.90 |
| FAM178A | family with sequence similarity 178, member A | 1.70 | 4.09 | 1.60 | 0.00 |
| FAM190B | family with sequence similarity 190, member B | 1.40 | 4.09 | 1.49 | 1.04 |
| FAM46A | family with sequence similarity 46, member A | 1.33 | 4.09 | 1.91 | 0.00 |
| FARP1 | FERM, RhoGEF (ARHGEF) and pleckstrin domain protein 1 (chondrocyte-derived) | 0.89 | 4.09 | 0.56 | 2.90 |
| FBXO42 | F-box protein 42 | 1.13 | 4.09 | 1.22 | 3.24 |
| FGFR1 | fibroblast growth factor receptor 1 | 1.15 | 4.09 | 1.21 | 3.24 |
| FH | fumarate hydratase | 0.90 | 0.00 | 0.74 | 2.90 |
| FLII | flightless I homolog (Drosophila) | 1.18 | 4.09 | 1.26 | 1.04 |
| FLNB | filamin B, beta | 0.86 | 0.00 | 0.76 | 2.90 |
| FNBP1 | formin binding protein 1 | 1.19 | 4.09 | 1.34 | 0.00 |
| FOXN3 | forkhead box N3 | 1.10 | 4.09 | 1.56 | 0.00 |
| FRY | furry homolog (Drosophila) | 1.23 | 4.09 | 1.77 | 0.00 |
| FUBP1 | far upstream element (FUSE) binding protein 1 | 1.25 | 4.09 | 1.67 | 0.00 |
| FXN | frataxin | 1.38 | 4.09 | 1.40 | 1.04 |

TABLE 4-continued

|  |  | GSE13449 | | GSE34512 | |
| --- | --- | --- | --- | --- | --- |
| Gene symbol | Gene title | Fold change | FDR (%) | Fold change | FDR (%) |
| FXR1 | fragile X mental retardation, autosomal homolog 1 | 1.17 | 4.09 | 1.22 | 0.00 |
| FZD5 | frizzled family receptor 5 | 1.15 | 4.09 | 6.75 | 0.00 |
| FZD6 | frizzled family receptor 6 | 1.13 | 4.09 | 1.55 | 0.00 |
| GALC | galactosylceramidase | 0.70 | 4.09 | 0.55 | 2.90 |
| GALK2 | galactokinase 2 | 1.52 | 4.09 | 1.40 | 0.00 |
| GALNT1 | UDP-N-acetyl-alpha-D-galactosamine:polypeptide N-acetylgalactosaminyltransferase 1 (GalNAc-T1) | 1.12 | 4.09 | 1.21 | 0.00 |
| GALNT12 | UDP-N-acetyl-alpha-D-galactosamine:polypeptide N-acetylgalactosaminyltransferase 12 (GalNAc-T12) | 1.13 | 4.09 | 1.36 | 0.00 |
| GALNT6 | UDP-N-acetyl-alpha-D-galactosamine:polypeptide N-acetylgalactosaminyltransferase 6 (GalNAc-T6) | 1.38 | 4.09 | 1.19 | 3.24 |
| GAR1 | GAR1 ribonucleoprotein homolog (yeast) | 1.21 | 4.09 | 1.28 | 0.00 |
| GATAD1 | GATA zinc finger domain containing 1 | 1.36 | 4.09 | 1.67 | 0.00 |
| GGH | gamma-glutamyl hydrolase (conjugase, folylpolygammaglutamyl hydrolase) | 0.75 | 0.00 | 0.53 | 2.90 |
| GGPS1 | geranylgeranyl diphosphate synthase 1 | 0.69 | 0.00 | 0.84 | 2.90 |
| GHITM | growth hormone inducible transmembrane protein | 1.13 | 4.09 | 1.19 | 0.00 |
| GIGYF2 | GRB10 interacting GYF protein 2 | 1.17 | 4.09 | 1.73 | 0.00 |
| GLRB | glycine receptor, beta | 0.87 | 0.00 | 0.72 | 2.90 |
| GM2A | GM2 ganglioside activator | 0.74 | 0.00 | 0.79 | 2.90 |
| GMCL1 | germ cell-less homolog 1 (*Drosophila*) | 0.66 | 0.00 | 0.90 | 2.90 |
| GNAI3 | guanine nucleotide binding protein (G protein), alpha inhibiting activity polypeptide 3 | 1.18 | 4.09 | 1.32 | 0.00 |
| GNAQ | guanine nucleotide binding protein (G protein), q polypeptide | 1.22 | 4.09 | 3.57 | 0.00 |
| GNAS | GNAS complex locus | 0.86 | 0.00 | 0.73 | 3.72 |
| GNB1 | guanine nucleotide binding protein (G protein), beta polypeptide 1 | 1.15 | 4.09 | 1.36 | 1.04 |
| GNG5 | guanine nucleotide binding protein (G protein), gamma 5 | 1.16 | 4.09 | 1.95 | 0.00 |
| GRSF1 | G-rich RNA sequence binding factor 1 | 1.11 | 4.09 | 1.41 | 0.00 |
| GSK3B | glycogen synthase kinase 3 beta | 1.22 | 4.09 | 1.52 | 0.00 |
| GSPT1 | G1 to S phase transition 1 | 1.20 | 4.09 | 1.71 | 0.00 |
| HES1 | hairy and enhancer of split 1, (*Drosophila*) | 1.16 | 4.09 | 1.26 | 0.00 |
| HEXIM1 | hexamethylene bis-acetamide inducible 1 | 1.27 | 4.09 | 1.92 | 0.00 |
| HIF1A | hypoxia inducible factor 1, alpha subunit (basic helix-loop-helix transcription factor) | 1.25 | 4.09 | 1.30 | 0.00 |
| HMGCS1 | 3-hydroxy-3-methylglutaryl-CoA synthase 1 (soluble) | 1.41 | 4.09 | 1.85 | 0.00 |
| HMGXN1 | high mobility group nucleosome binding domain 1 | 1.11 | 4.09 | 1.31 | 0.00 |
| HMGXB4 | HMG box domain containing 4 | 1.12 | 4.09 | 1.40 | 0.00 |
| HN1 | hematological and neurological expressed 1 | 1.13 | 4.09 | 1.43 | 0.00 |
| HN1L | hematological and neurological expressed 1-like | 0.87 | 4.09 | 0.51 | 2.90 |
| HNRNPA2B1 | heterogeneous nuclear ribonucleoprotein A2/B1 | 1.16 | 4.09 | 1.12 | 1.04 |
| HNRNPH1 | heterogeneous nuclear ribonucleoprotein H1 (H) | 1.22 | 4.09 | 1.42 | 0.00 |
| HNRNPM | heterogeneous nuclear ribonucleoprotein M | 1.11 | 4.09 | 1.30 | 0.00 |
| HNRNPR | heterogeneous nuclear ribonucleoprotein R | 1.20 | 4.09 | 1.50 | 0.00 |
| HNRNPU | heterogeneous nuclear ribonucleoprotein U (scaffold attachment factor A) | 1.23 | 4.09 | 1.56 | 0.00 |
| HSPA4 | heat shock 70 kDa protein 4 | 1.11 | 4.09 | 1.55 | 0.00 |
| HSPA9 | heat shock 70 kDa protein 9 (mortalin) | 1.22 | 4.09 | 1.70 | 0.00 |
| HSPB1 | heat shock 27 kDa protein 1 | 1.12 | 4.09 | 1.40 | 1.04 |
| HSPB11 | heat shock protein family B (small), member 11 | 1.14 | 4.09 | 1.61 | 0.00 |
| HSPBAP1 | HSPB (best shock 27 kDa) associated protein 1 | 0.81 | 4.09 | 0.81 | 2.90 |
| IBTK | inhibitor of Bruton agammaglobulinemia tyrosine kinase | 1.21 | 4.09 | 2.78 | 0.00 |
| IFI30 | interferon gamma-inducible protein 30 | 1.75 | 4.09 | 4.42 | 0.00 |
| IFIH1 | interferon induced with helicase C domain 1 | 1.50 | 4.09 | 2.40 | 0.00 |
| IGFBP5 | insulin-like growth factor binding protein 5 | 0.63 | 0.00 | 0.90 | 2.90 |
| INSIG1 | insulin induced gene 1 | 1.40 | 4.09 | 1.41 | 0.00 |
| INTS6 | integrator complex subunit 6 | 1.22 | 4.09 | 1.79 | 0.00 |
| IPO9 | importin 9 | 0.86 | 4.09 | 0.42 | 2.90 |
| ITGAE | integrin, alpha E (antigen CD103, human mucosal lymphocyte antigen 1; alpha polypeptide) | 0.87 | 0.00 | 0.74 | 2.90 |
| ITGB4 | integrin, beta 4 | 1.50 | 4.09 | 1.12 | 0.00 |
| ITPKC | inositol-trisphosphate 3-kinase C | 1.11 | 4.09 | 2.05 | 0.00 |
| ITPR1 | inositol 1,4,5-trisphosphate receptor, type 1 | 0.56 | 0.00 | 0.89 | 2.90 |
| ITSN1 | intersectin 1 (SH3 domain protein) | 1.45 | 4.09 | 1.33 | 0.00 |
| ITSN2 | intersectin 2 | 1.39 | 4.09 | 1.36 | 0.00 |
| IVD | isovaleryl-CoA dehydrogenase | 1.25 | 4.09 | 1.82 | 0.00 |
| JUP | junction plakoglobin | 1.11 | 4.09 | 1.51 | 0.00 |
| KCTD3 | potassium channel tetramerisation domain containing 3 | 1.12 | 4.09 | 1.22 | 1.04 |
| KDM3B | lysine (K)-specific demethylase 3B | 1.25 | 4.09 | 1.40 | 1.04 |
| KEAP1 | kelch-like ECH-associated protein 1 | 1.17 | 4.09 | 1.45 | 1.04 |
| KIAA1324 | KIAA1324 | 0.82 | 0.00 | 0.60 | 2.90 |
| KITLG | KIT ligand | 1.45 | 4.09 | 1.21 | 0.00 |
| KRIT1 | KRIT1, ankyrin repeat containing | 1.33 | 4.09 | 1.42 | 0.00 |
| LAMC1 | laminin, gamma 1 (formerly LAMB2) | 0.90 | 0.00 | 0.76 | 3.72 |

TABLE 4-continued

| Gene symbol | Gene title | GSE13449 Fold change | GSE13449 FDR (%) | GSE34512 Fold change | GSE34512 FDR (%) |
|---|---|---|---|---|---|
| LARP1 | La ribonucleoprotein domain family, member 1 | 1.17 | 4.09 | 1.15 | 0.00 |
| LARP4 | La ribonucleoprotein domain family, member 4 | 1.25 | 4.09 | 1.34 | 0.00 |
| LDHA | lactate dehydrogenase A | 1.11 | 4.09 | 1.19 | 0.00 |
| LEPROTL1 | leptin receptor overlapping transcript-like 1 | 0.87 | 0.00 | 0.50 | 2.90 |
| LGALS3BP | lectin, galactoside-binding, soluble, 3 binding protein | 1.74 | 4.09 | 1.86 | 0.00 |
| LIFR | leukemia inhibitory factor receptor alpha | 1.33 | 4.09 | 3.25 | 0.00 |
| LMNA | lamin A/C | 1.19 | 4.09 | 1.56 | 1.04 |
| LPCAT1 | lysophosphatidylcholine acyltransferase 1 | 1.13 | 4.09 | 1.54 | 0.00 |
| LPIN2 | lipin 2 | 1.16 | 4.09 | 2.24 | 0.00 |
| LRFN4 | leucine rich repeat and fibronectin type III domain containing 4 | 1.11 | 4.09 | 1.82 | 0.00 |
| LRP8 | low density lipoprotein receptor-related protein 8, apolipoprotein e receptor | 1.39 | 4.09 | 1.11 | 1.04 |
| LRRFIP1 | leucine rich repeat (in FLII) intracting protein 1 | 1.42 | 4.09 | 1.22 | 0.00 |
| LSM14A | LSM14A, SCD6 homolog A (S. cerevisiae) | 1.15 | 4.09 | 1.50 | 0.00 |
| LUC7L3 | LUC7-like 3 (S. cerevisiae) | 1.26 | 4.09 | 1.27 | 0.00 |
| LYRM1 | LYR motif containing 1 | 1.31 | 4.09 | 1.26 | 0.00 |
| MALT1 | mucosa associated lymphoid tissue lymphoma translocation gene 1 | 1.19 | 4.09 | 2.19 | 0.00 |
| MAP2K6 | mitogen-activated protein kinase kinase 6 | 1.21 | 4.09 | 1.62 | 0.00 |
| MARC2 | mitochondrial amidoxime reducing component 2 | 0.87 | 0.00 | 0.89 | 2.90 |
| MBNL2 | muscleblind-like splicing regulator 2 | 1.54 | 4.09 | 1.37 | 0.00 |
| MBOAT7 | membrane bound O-acyltransferase domain containing 7 | 1.20 | 4.09 | 1.58 | 0.00 |
| MCFD2 | multiple coagulation factor deficiency 2 | 1.32 | 4.09 | 1.14 | 0.00 |
| MED17 | mediator complex subunit 17 | 0.90 | 0.00 | 0.77 | 3.61 |
| MED6 | mediator complex subunit 6 | 1.32 | 4.09 | 1.43 | 0.00 |
| MEF2A | myocyte enhancer factor 2A | 0.90 | 0.00 | 0.77 | 2.90 |
| METTL7A | methyltransferase like 7A | 1.25 | 4.09 | 2.18 | 0.00 |
| MFHAS1 | malignant fibrous histiocytoma amplified sequence 1 | 1.50 | 4.09 | 1.51 | 0.00 |
| MGA | MAX gene associated | 1.25 | 4.09 | 1.14 | 0.00 |
| MGEA5 | meningioma expressed antigen 5 (hyaluronidase) | 1.24 | 4.09 | 1.21 | 0.00 |
| MORC3 | MORC family CW-type zinc finger 3 | 1.23 | 4.09 | 1.18 | 0.00 |
| MRPS35 | mitochondrial ribosomal protein S35 | 1.18 | 4.09 | 1.53 | 1.04 |
| MRTO4 | mRNA turnover 4 homolog (S. cerevisiae) | 1.17 | 4.09 | 1.34 | 1.04 |
| MSL1 | male-specific lethal 1 homolog (Drosophila) | 1.15 | 4.09 | 1.43 | 0.00 |
| MT1F | metallothionein 1F | 1.41 | 4.09 | 1.38 | 0.00 |
| MT1G | metallothionein 1G | 1.21 | 4.09 | 1.21 | 0.00 |
| MT1P2 | metallothionein 1 pseudogene 2 | 1.44 | 4.09 | 1.29 | 0.00 |
| MT1X | metallothionein 1X | 1.44 | 4.09 | 1.31 | 0.00 |
| MT2A | metallothionein 2A | 1.46 | 4.09 | 1.22 | 0.00 |
| MTDH | metadherin | 1.17 | 4.09 | 1.12 | 0.00 |
| MTO1 | mitochondrial translation optimization 1 homolog (S. cerevisiae) | 1.18 | 4.09 | 1.18 | 0.00 |
| MTR | 5-methyltetrahydrofolate-homocysteine methyltransferase | 1.43 | 4.09 | 2.21 | 0.00 |
| MTUS1 | microtubule associated tumor suppressor 1 | 1.34 | 4.09 | 3.09 | 0.00 |
| MYOF | myoferlin | 1.34 | 4.09 | 1.17 | 0.00 |
| NAB1 | NGFI-A binding protein 1 (EGR1 binding protein 1) | 0.64 | 0.00 | 0.83 | 2.90 |
| NACC2 | NACC family member 2, BEN and BTB (POZ) domain containing | 1.24 | 4.09 | 1.41 | 1.04 |
| NAMPT | nicotinamide phosphoribosyltransferase | 0.09 | 0.00 | 0.02 | 2.90 |
| NBAS | neuroblastoma amplified sequence | 0.88 | 4.09 | 0.85 | 3.72 |
| NBN | nibrin | 1.12 | 4.09 | 1.48 | 0.00 |
| NCL | nucleolin | 1.11 | 4.09 | 1.32 | 0.00 |
| NCOA1 | nuclear receptor coactivator 1 | 1.32 | 4.09 | 4.84 | 0.00 |
| NCOR1 | nuclear receptor corepressor 1 | 1.36 | 4.09 | 1.52 | 0.00 |
| NET1 | neuroepithelial cell transforming 1 | 1.14 | 4.09 | 2.37 | 0.00 |
| NFATC2IP | nuclear factor of activated T-cells, cytoplasmic, calcineurin-dependant 2 interacting protein | 1.15 | 4.09 | 3.54 | 0.00 |
| NFIB | nuclear factor I/B | 1.62 | 4.09 | 1.75 | 0.00 |
| NFKBIA | nuclear factor of kappa light polypeptide gene enhancer in B-cells inhibitor, alpha | 1.21 | 4.09 | 1.25 | 1.04 |
| NINJ1 | ninjurin 1 | 1.22 | 4.09 | 1.49 | 0.00 |
| NLK | nemo-like kinase | 1.38 | 4.09 | 1.26 | 0.00 |
| NRCAM | neuronal cell adhesion molecule | 0.67 | 0.00 | 0.56 | 2.90 |
| NUPL1 | nucleoporin like 1 | 1.65 | 4.09 | 1.58 | 0.00 |
| NUSAP1 | nucleolar and spindle associated protein 1 | 1.11 | 4.09 | 1.33 | 1.04 |
| OPA1 | optic atrophy 1 (autosomal dominant) | 1.43 | 4.09 | 1.28 | 0.00 |
| OPN3 | opsin 3 | 1.14 | 4.09 | 1.66 | 0.00 |
| OSBPL10 | oxysterol binding protein-like 10 | 1.18 | 4.09 | 1.40 | 0.00 |
| OSMR | oncostatin M receptor | 1.74 | 4.09 | 2.90 | 0.00 |
| PAICS | phosphoribosylaminoimidazole carboxylase, phosphoribosylaminoimidazole succinocarboxamide synthetase | 1.18 | 4.09 | 4.75 | 0.00 |
| PAK2 | p21 protein (Cdc42/Rac)-activated kinase 2 | 1.15 | 4.09 | 1.88 | 0.00 |

TABLE 4-continued

| | | GSE13449 | | GSE34512 | |
|---|---|---|---|---|---|
| Gene symbol | Gene title | Fold change | FDR (%) | Fold change | FDR (%) |
| PAPOLA | poly(A) polymerase alpha | 1.19 | 4.09 | 1.57 | 0.00 |
| PAPSS1 | 3'-phosphoadenosine 5'-phosphosulfate synthase 1 | 0.87 | 0.00 | 0.86 | 3.72 |
| PAPSS2 | 3'-phosphoadenosine 5'-phosphosulfate synthase 2 | 0.57 | 0.00 | 0.78 | 3.72 |
| PBX2 | pre-B-cell leukemia homeobox 2 | 1.33 | 4.09 | 1.90 | 0.00 |
| PCMT1 | protein-L-isoaspartate (D-aspartate) O-methyltransferase | 1.11 | 4.09 | 1.26 | 0.00 |
| PDLIM7 | PDZ and LIM domain 7 (enigma) | 1.13 | 4.09 | 2.21 | 0.00 |
| PHACTR2 | phosphatase and actin regulator 2 | 1.51 | 4.09 | 1.24 | 0.00 |
| PHF20L1 | PHD finger protein 20-like 1 | 1.25 | 4.09 | 1.44 | 1.04 |
| PHKB | phosphorylase kinase, beta | 0.86 | 0.00 | 0.76 | 2.90 |
| PHLDA3 | pleckstrin homology-like domain, family A, member 3 | 1.13 | 4.09 | 1.60 | 0.00 |
| PHTF1 | putative homeodomain transcription factor 1 | 0.84 | 0.00 | 0.82 | 2.90 |
| PLAS1 | protein inhibitor of activated STAT, 1 | 1.20 | 4.09 | 1.66 | 0.00 |
| PIK3R3 | phosphoinositide-3-kinase, regulatory subunit 3 (gamma) | 1.22 | 4.09 | 1.51 | 0.00 |
| PIP4K2B | phosphatidylinositol-5-phosphate 4-kinase, type II, beta | 1.60 | 4.09 | 1.30 | 1.04 |
| PITRM1 | pitrilysin metallopeptidase 1 | 1.13 | 4.09 | 1.58 | 0.00 |
| PNN | pinin, desmosome associated protein | 1.45 | 4.09 | 1.20 | 0.00 |
| PNO1 | partner of NOB1 homolog (S. cerevisiae) | 1.10 | 4.09 | 1.31 | 0.00 |
| PPAP2B | phosphatidic acid phosphatase type 2B | 1.15 | 4.09 | 1.50 | 0.00 |
| PPME1 | protein phosphatase methylesterase 1 | 0.82 | 0.00 | 0.71 | 2.90 |
| PPP1R13L | protein phosphatase 1, regulatory subunit 13 like | 0.84 | 0.00 | 0.84 | 3.72 |
| PPP1R3C | protein phosphatase 1, regulatory subunit 3C | 1.40 | 4.09 | 5.72 | 0.00 |
| PPP2CA | protein phosphatase 2, catalytic subunit, alpha isozyme | 1.17 | 4.09 | 1.28 | 0.00 |
| PPP2R1B | protein phosphatase 2, regulatory subunit A, beta | 1.23 | 4.09 | 1.28 | 1.04 |
| PPP3CA | protein phosphatase 3, catalytic subunit, alpha isozyme | 1.18 | 4.09 | 1.26 | 0.00 |
| PPP3CB | protein phosphatase 3, catalytic subunit, beta isozyme | 0.86 | 0.00 | 0.42 | 2.90 |
| PPP6R3 | protein phosphatase 6, regulatory subunit 3 | 1.18 | 4.09 | 1.17 | 1.04 |
| PRCC | papillary renal cell carcinoma (translocation-associated) | 1.19 | 4.09 | 1.55 | 1.04 |
| PREPL | prolyl endopeptidase-like | 0.84 | 0.00 | 0.81 | 3.61 |
| PRKAR2A | protein kinase, cAMP-dependent, regulatory, type II, alpha | 1.18 | 4.09 | 1.45 | 0.00 |
| PRNP | prion protein | 0.85 | 0.00 | 0.82 | 3.72 |
| PROSER1 | proline and serine rich 1 | 1.17 | 4.09 | 1.40 | 0.00 |
| PRPF39 | PRP39 pre-mRNA processing factor 39 homolog (S. cerevisiae) | 1.28 | 4.09 | 1.21 | 1.04 |
| PRPF40A | PRP40 pre-mRNA processing factor 40 homolog A (S. cerevisiae) | 1.31 | 4.09 | 1.31 | 0.00 |
| PRPF4B | PRP4 pre-mRNA processing factor 4 homolog B (yeast) | 1.32 | 4.09 | 1.47 | 0.00 |
| PRR11 | proline-rich 11 | 1.31 | 4.09 | 2.43 | 0.00 |
| PRRC1 | proline-rich coiled-coil 1 | 1.17 | 4.09 | 1.14 | 1.04 |
| PRRC2A | proline-rich coiled-coil 2A | 1.22 | 4.09 | 1.68 | 0.00 |
| PSMA1 | proteasome (prosome, macropain) subunit, alpha type, 1 | 1.11 | 4.09 | 1.16 | 0.00 |
| PSMB2 | proteasome (prosome, macropain) subunit, beta type, 2 | 1.14 | 4.09 | 1.40 | 0.00 |
| PSMC1 | proteasome (prosome, macropain) 26S subunit, ATPase, 1 | 1.10 | 4.09 | 1.31 | 0.00 |
| PSMD11 | proteasome (prosome, macropain) 26S subunit, non-ATPase, 11 | 1.17 | 4.09 | 1.28 | 0.00 |
| PSMD12 | proteasome (prosome, macropain) 26S subunit, non-ATPase, 12 | 1.12 | 4.09 | 1.54 | 0.00 |
| PUM2 | pumilio homolog 2 (Drosophila) | 1.15 | 4.09 | 1.18 | 1.04 |
| QKI | QKI, KH domain containing, RNA binding | 1.22 | 4.09 | 1.44 | 0.00 |
| RAB11FIP1 | RAB11 family interacting protein 1 (class I) | 1.13 | 4.09 | 1.30 | 0.00 |
| RAB21 | RAB21, member RAS oncogene family | 1.14 | 4.09 | 1.37 | 0.00 |
| RABEP1 | rabaptin, RAB GTPase binding effector protein 1 | 1.15 | 4.09 | 1.21 | 0.00 |
| RABL3 | RAB, member of RAS oncogene family-like 3 | 1.20 | 4.09 | 1.55 | 0.00 |
| RAD23B | RAD23 homolog B (S. cerevisiae) | 1.15 | 4.09 | 1.21 | 1.04 |
| RBBP6 | retinoblastoma binding protein 6 | 1.87 | 4.09 | 3.86 | 0.00 |
| RBBP8 | retinoblastoma binding protein 8 | 0.88 | 0.00 | 0.84 | 2.90 |
| RBM25 | RNA binding motif protein 25 | 1.33 | 4.09 | 1.36 | 0.00 |
| RBM39 | RNA binding motif protein 39 | 1.18 | 4.09 | 1.26 | 0.00 |
| RBM4 | RNA binding motif protein 4 | 0.87 | 0.00 | 0.79 | 2.90 |
| RBMS1 | RNA binding motif, single stranded interacting protein 1 | 1.15 | 4.09 | 1.68 | 0.00 |
| RBPJ | recombination signal binding protein for immunoglobulin kappa J region | 1.25 | 4.09 | 2.32 | 0.00 |
| RCN1 | reticulocalbin 1, EF-hand calcium binding domain | 1.16 | 4.09 | 1.22 | 0.00 |
| RFX7 | regulatory factor X, 7 | 1.43 | 4.09 | 1.74 | 0.00 |
| RHEB | Ras homolog enriched in brain | 1.20 | 4.09 | 1.51 | 0.00 |
| RING1 | ring finger protein 1 | 1.14 | 4.09 | 1.34 | 0.00 |
| RLN2 | relaxin 2 | 0.78 | 0.00 | 0.56 | 2.90 |
| RND3 | Rho family GTPase 3 | 1.69 | 4.09 | 1.45 | 0.00 |
| RNF6 | ring finger protein (C3H2C3 type) 6 | 1.29 | 4.09 | 1.37 | 0.00 |
| RRAGC | Ras-related GTP binding C | 1.14 | 4.09 | 1.37 | 0.00 |
| RRAS2 | related RAS viral (r-ras) oncogene homolog 2 | 0.86 | 4.09 | 0.88 | 3.72 |
| RREB1 | ras responsive element binding protein 1 | 1.12 | 4.09 | 1.52 | 0.00 |
| RSL1D1 | ribosomal L1 domain containing 1 | 1.13 | 4.09 | 1.40 | 0.00 |
| RSRC2 | arginine/serine-rich coiled-coil 2 | 1.23 | 4.09 | 1.42 | 0.00 |

TABLE 4-continued

|  |  | GSE13449 | | GSE34512 | |
| --- | --- | --- | --- | --- | --- |
| Gene symbol | Gene title | Fold change | FDR (%) | Fold change | FDR (%) |
| RUFY1 | RUN and FYVE domain containing 1 | 1.14 | 4.09 | 1.45 | 0.00 |
| RUFY3 | RUN and FYVE domain containing 3 | 1.42 | 4.09 | 1.86 | 0.00 |
| S100A10 | S100 calcium binding protein A10 | 1.12 | 4.09 | 1.36 | 3.24 |
| SAFB | scaffold attachmemt factor B | 1.11 | 4.09 | 2.16 | 0.00 |
| SCAF4 | SR-related CTD-associated factor 4 | 1.12 | 4.09 | 1.11 | 0.00 |
| SCARB2 | scavenger receptor class B, member 2 | 1.20 | 4.09 | 1.83 | 0.00 |
| SDC2 | syndecan 2 | 0.87 | 0.00 | 0.64 | 2.90 |
| SEC14L1 | SEC14-like 1 (*S. cerevisiae*) | 1.21 | 4.09 | 1.74 | 0.00 |
| SEC24D | SEC24 family, member D (*S. cerevisiae*) | 0.81 | 0.00 | 0.67 | 3.72 |
| SEC61G | Sec61 gamma subunit | 1.16 | 4.09 | 1.68 | 0.00 |
| SEMA4C | sema domain, immunoglobulin domain (Ig), transmembrane domain (TM) and short cytoplasmic domain (semaphorin) 4C | 1.24 | 4.09 | 1.86 | 0.00 |
| SENP6 | SUMO1/sentrin specific peptidase 6 | 1.18 | 4.09 | 1.21 | 0.00 |
| SEP15 | 15 kDa selenoprotein | 1.15 | 4.09 | 1.31 | 0.00 |
| SEPT7 | septin 7 | 1.15 | 4.09 | 1.17 | 0.00 |
| SEPT8 | septin 8 | 0.85 | 0.00 | 0.77 | 2.90 |
| SERINC3 | serine incorporator 3 | 1.27 | 4.09 | 1.18 | 0.00 |
| SET | SET nuclear oncogene | 1.21 | 4.09 | 1.32 | 0.00 |
| SETD1B | SET domain containing 1B | 1.12 | 4.09 | 1.27 | 0.00 |
| SETD5 | SET domain containing 5 | 1.16 | 4.09 | 1.43 | 0.00 |
| SFPQ | splicing factor proline/glutamine-rich | 1.15 | 4.09 | 1.77 | 0.00 |
| SGPL1 | sphingosine-1-phosphate lyase 1 | 0.79 | 0.00 | 0.34 | 2.90 |
| SGPP1 | sphingosine-1-phosphate phosphatase 1 | 1.12 | 4.09 | 8.13 | 0.00 |
| SH3GLB2 | SH3-domain GRB2-like endophilin B2 | 1.21 | 4.09 | 1.58 | 0.00 |
| SH3YL1 | SH3 domain containing, Ysc84-like 1 (*S. cerevisiae*) | 0.87 | 0.00 | 0.85 | 3.61 |
| SIRT1 | sirtuin 1 | 1.37 | 4.09 | 1.36 | 0.00 |
| SKIL | SKI-like oncogene | 1.11 | 4.09 | 1.54 | 0.00 |
| SLC22A4 | solute carrier family 22 (organic cation/ergothioneine transporter), member 4 | 1.29 | 4.09 | 1.38 | 0.00 |
| SLC25A36 | solute carrier family 25 (pyrimidine nucleotide carrier), member 36 | 1.33 | 4.09 | 1.40 | 1.04 |
| SLC25A40 | solute carrier family 25, member 40 | 0.89 | 0.00 | 0.50 | 2.90 |
| SLC26A2 | solute carrier family 26 (sulfate transporter), member 2 | 1.49 | 4.09 | 5.70 | 0.00 |
| SLC2A10 | solute carrier family 2 (facilitated glucose transporter), member 10 | 1.35 | 4.09 | 1.41 | 0.00 |
| SLC31A1 | solute carrier family 31 (copper transporters), member 1 | 1.17 | 4.09 | 1.16 | 3.24 |
| SLC38A2 | solute carrier family 38, member 2 | 1.21 | 4.09 | 1.43 | 0.00 |
| SLC7A1 | solute carrier family 7 (cationic amino acid transporter, y+ system), member 1 | 0.80 | 0.00 | 0.64 | 2.90 |
| SLMO2 | slowmo homolog 2 (*Drosophila*) | 1.14 | 4.09 | 1.71 | 0.00 |
| SMARCA4 | SWI/SNF related, maitrix associated, actin dependent regulator of chromatin, subfamily a, member 4 | 1.12 | 4.09 | 1.64 | 0.00 |
| SMEK1 | SMEK homolog 1, suppressor of mek1 (*Dictyostelium*) | 1.31 | 4.09 | 1.72 | 0.00 |
| SNCG | synuclein, gamma (breast cancer-specific protein 1) | 2.34 | 4.09 | 1.94 | 1.04 |
| SNRPA1 | small nuclear ribonucleoprotein polypeptide A' | 1.16 | 4.09 | 1.25 | 0.00 |
| SNTB2 | syntrophin, beta 2 (dystrophin-associated protein A1, 59 kDa, basic component 2) | 1.28 | 4.09 | 1.35 | 0.00 |
| SNX2 | sorting nexin 2 | 1.15 | 4.09 | 1.70 | 0.00 |
| SORD | sorbitol dehydrogenase | 1.10 | 4.09 | 2.85 | 0.00 |
| SOWAHC | sosondowah ankyrin repeat domain family member C | 1.29 | 4.09 | 1.18 | 0.00 |
| SPG20 | spastic paraplegia 20 (Troyer syndrome) | 1.17 | 4.09 | 1.20 | 0.00 |
| SREK1 | splicing regulatory glutamine/lysine-rich protein 1 | 1.46 | 4.09 | 1.34 | 0.00 |
| SRGAP2 | SLIT-ROBO Rho GTPase activating protein 2 | 1.20 | 4.09 | 1.52 | 0.00 |
| SRM | spermidene synthase | 1.13 | 4.09 | 1.69 | 1.04 |
| SS18 | synovial sarcoma translocation, chromosome 18 | 1.26 | 4.09 | 2.08 | 0.00 |
| SSH1 | slingshot homolog 1 (*Drosophila*) | 0.81 | 0.00 | 0.69 | 2.90 |
| ST13 | suppression of tumorigenicity 13 (colon carcinoma) (Hsp70 interacting protein) | 1.11 | 4.09 | 1.42 | 0.00 |
| STAMBP | STAM binding protein | 0.82 | 0.00 | 0.74 | 3.61 |
| STAU2 | staufen, RNA binding protein, homolog 2 (*Drosophila*) | 0.74 | 0.00 | 0.69 | 2.90 |
| STC2 | stanniocalcin 2 | 1.16 | 4.09 | 1.18 | 0.00 |
| STEAP3 | STEAP family member 3, metalloreductase | 1.32 | 4.09 | 2.04 | 0.00 |
| STRN3 | striatin, calmodulin bindin protein 3 | 1.19 | 4.09 | 1.79 | 0.00 |
| STX3 | syntaxin 3 | 1.29 | 4.09 | 2.37 | 0.00 |
| SYNCRIP | synaptotagmin binding, cytoplasmic, RNA interacting protein | 1.12 | 4.09 | 1.39 | 0.00 |
| TAB2 | TGF-beta activated kinase 1/MAP3K7 binding protein 2 | 1.27 | 4.09 | 1.32 | 1.04 |
| TAF1B | TATA box binding protein (TBP)-associated factor, RNA polymerase I, B, 63 kDa | 0.88 | 4.09 | 0.85 | 2.90 |
| TAPBP | TAP binding protein (tapasin) | 1.11 | 4.09 | 2.19 | 0.00 |
| TBC1D2 | TBC1 domain family, member 2 | 0.87 | 0.00 | 0.88 | 3.72 |

TABLE 4-continued

| | | GSE13449 | | GSE34512 | |
|---|---|---|---|---|---|
| Gene symbol | Gene title | Fold change | FDR (%) | Fold change | FDR (%) |
| TBL1XR1 | transducin (beta)-like 1 X-linked receptor 1 | 1.45 | 4.09 | 1.51 | 0.00 |
| TCERG1 | transcription elongation regulator 1 | 1.62 | 4.09 | 1.55 | 0.00 |
| TCF3 | transcription factor 3 (E2A immunoglobulin enhancer binding factors E12/E47) | 1.29 | 4.09 | 1.29 | 0.00 |
| TCF7L2 | transcription factor 7-like 2 (T-cell specific, HMG-box) | 0.82 | 0.00 | 0.87 | 2.90 |
| TFAM | transcription factor A, mitochondrial | 1.31 | 4.09 | 1.89 | 0.00 |
| TFPI | tissue factor pathway inhibitor (lipoprotein-associated coagulation inhibitor) | 3.89 | 4.09 | 1.75 | 0.00 |
| TGFB2 | transforming growth factor, beta 2 | 0.19 | 0.00 | 0.52 | 2.90 |
| TGFBR2 | transforming growth factor, beta receptor II (70/80 kDa) | 1.14 | 4.09 | 1.34 | 0.00 |
| THUMPD1 | THUMP domain containing 1 | 1.18 | 4.09 | 1.26 | 0.00 |
| TJP1 | tight junction protein 1 (zona occludens 1) | 1.30 | 4.09 | 1.30 | 0.00 |
| TMCC1 | transmembrane and coiled-coil domain family 1 | 1.16 | 4.09 | 1.50 | 0.00 |
| TMED2 | transmembrane emp24 domain trafficking protein 2 | 1.15 | 4.09 | 1.51 | 0.00 |
| TMED5 | transmembrane emp24 protein transport domain containing 5 | 1.21 | 4.09 | 1.48 | 0.00 |
| TMF1 | TATA element modulatory factor 1 | 1.32 | 4.09 | 1.35 | 0.00 |
| TMOD3 | tropomodulin 3 (ubiquitous) | 2.29 | 4.09 | 1.25 | 1.04 |
| TNFRSF10B | tumor necrosis factor receptor superfamily, member 10b | 1.15 | 4.09 | 3.01 | 0.00 |
| TNPO1 | transportin 1 | 1.11 | 4.09 | 1.19 | 1.04 |
| TOB2 | transducer of ERBB2, 2 | 1.72 | 4.09 | 1.93 | 0.00 |
| TOP1 | topoisomerase (DNA) I | 1.27 | 4.09 | 1.13 | 1.04 |
| TPM4 | tropomyosin 4 | 1.45 | 4.09 | 1.67 | 0.00 |
| TRAF3IP2 | TRAF3 interacting protein 2 | 1.14 | 4.09 | 1.23 | 1.04 |
| TRAF5 | TNF receptor-assiciated factor 5 | 1.36 | 4.09 | 1.21 | 0.00 |
| TRAK1 | trafficking protein, kinesis binding 1 | 0.65 | 0.00 | 0.72 | 2.90 |
| TRAM2 | translocation associated membrane protein 2 | 1.19 | 4.09 | 1.34 | 0.00 |
| TRIM13 | tripartite motif containing 23 | 0.86 | 0.00 | 0.66 | 2.90 |
| TRIM33 | tripartite motif containing 33 | 1.15 | 4.09 | 1.14 | 0.00 |
| TRMT1L | tRNA methyltransferase 1 homolog (*S. cerevisiae*)-like | 1.40 | 4.09 | 3.30 | 0.00 |
| TROVE2 | TROVE domain family, member 2 | 1.70 | 4.05 | 1.20 | 0.00 |
| TSN | translin | 0.88 | 0.00 | 0.80 | 3.72 |
| TSPAN4 | tetraspanin 4 | 1.17 | 4.05 | 2.64 | 0.00 |
| TTC37 | tetratricopeptide repeat domain 37 | 1.20 | 4.09 | 1.28 | 0.00 |
| TTF1 | transcription termination factor, RNA polymerase I | 1.51 | 4.09 | 1.21 | 0.00 |
| TUSC2 | tumor suppressor candidate 2 | 1.98 | 4.09 | 1.94 | 0.00 |
| U2SURP | U2 snRNP-associated SURP domain containing | 1.33 | 4.09 | 1.62 | 0.00 |
| UBA2 | ubiquitin-like modifier activating enzyme 2 | 0.88 | 0.00 | 0.83 | 3.61 |
| UBE2H | ubiquitin-conjugating enzyme E2H | 1.19 | 4.09 | 1.28 | 0.00 |
| UBE2K | ubiquitin-conjugating enzyme E2K | 1.11 | 4.09 | 1.11 | 0.00 |
| UBE3A | ubiquitin protein ligase E3A | 1.19 | 4.09 | 1.25 | 0.00 |
| USO1 | USO1 vesicle docking protein homolog (yeast) | 1.29 | 4.09 | 1.14 | 0.00 |
| USP32 | ubiquitin specific peptidase 32 | 1.21 | 4.09 | 1.50 | 0.00 |
| USP48 | ubiquitin specific peptidase 48 | 1.20 | 4.09 | 1.37 | 0.00 |
| VAMP4 | vesicle-associated membrane protein 4 | 0.72 | 0.00 | 0.78 | 3.72 |
| VCP | valosin containing protein | 1.15 | 4.09 | 1.65 | 0.00 |
| VEGFC | vascular endothelial growth factor C | 0.90 | 0.00 | 0.71 | 2.90 |
| WDR26 | WD repeat domain 26 | 1.16 | 4.09 | 1.71 | 0.00 |
| WHSC1 | Wolf-Hirschhorn syndrome candidate 1 | 1.15 | 4.09 | 1.43 | 0.00 |
| WRB | tryptophan rich basic protein | 0.88 | 0.00 | 0.79 | 2.90 |
| YAP1 | Yes-associated protein 1 | 1.24 | 4.09 | 2.09 | 0.00 |
| YTHDF3 | YTH domain family, member 3 | 1.10 | 4.09 | 3.79 | 0.00 |
| ZC3H15 | zinc finger CCCH-type containing 15 | 1.24 | 4.09 | 1.17 | 1.04 |
| ZC3HAV1 | zinc finger CCCH-type, antiviral 1 | 1.27 | 4.09 | 1.55 | 0.00 |
| ZFAND6 | zinc finger AN1-type domain 6 | 1.11 | 4.09 | 1.32 | 0.00 |
| ZFHX3 | zinc finger homeobox 3 | 1.60 | 4.09 | 1.73 | 0.00 |
| ZFP36L1 | zinc finger protein 36, C3H type-like 1 | 0.88 | 0.00 | 0.65 | 3.72 |
| ZMIZ2 | zinc finger, MIZ-type containing 2 | 0.85 | 0.00 | 0.87 | 3.72 |
| ZNF12 | zinc finger protein 12 | 1.21 | 4.09 | 1.49 | 0.00 |
| ZNF136 | zinc finger protein 136 | 1.20 | 4.09 | 1.57 | 0.00 |
| ZNF160 | zinc finger protein 160 | 1.21 | 4.09 | 1.34 | 0.00 |
| ZNF174 | zinc finger protein 174 | 1.16 | 4.09 | 4.31 | 0.00 |
| ZNF238 | zinc finger protein 238 | 0.71 | 0.00 | 0.75 | 2.90 |
| ZNF329 | zinc finger protein 329 | 1.26 | 4.09 | 1.79 | 0.00 |
| ZNF432 | zinc finger protein 432 | 1.24 | 4.09 | 1.36 | 0.00 |
| ZNF467 | zinc finger protein 467 | 1.45 | 4.09 | 1.15 | 1.04 |
| ZNF84 | zinc finger protein 84 | 1.32 | 4.09 | 1.24 | 0.00 |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A method of detecting gene expression in a tissue sample from a subject, comprising:

assaying a tissue sample from a subject for the quantity of gene expression of 5 to 39 genes, wherein said 5 genes are DONSON, GGH, MT1G, PPME1, and SGPL1, using a assay that comprises the steps of i) contacting a nucleic acid in said sample with detection reagents selected from the group consisting of nucleic acid primers, probes, or pairs of primers that specifically bind to said 5 to 39 genes; and ii) detecting the presence of a complex between said detection reagent and said nucleic acid, wherein the method detects the expression of the 5 to 39 genes, and no more than the 5 to 39 genes.

2. The method of claim 1, wherein said tissue sample is lung cancer tissue or breast cancer tissue.

3. The method of claim 1, wherein said 5 to 39 genes further comprise one or more genes selected from the group consisting of ADK, AP2B1, AVL9, CANX, DBT, DHRS7, FAM190B, FGFR1, FOXN3, FZD5, GM2A, IGFBP5, ITSN2, LAMC1, LIFR, METTL7A, MT1F, MT1P2, MT1X, MT2A, NAB1, NCOA1, NCOR1, PAPOLA, PPP1R13L, PRKAR2A, RABEP1, RBBP8, SIRT1, SNX2, SREK1, TAF1B, TMED5, and ZMIZ2.

4. The method of claim 1, wherein said subject is a subject diagnosed with cancer.

* * * * *